(12) United States Patent
Suddaby

(10) Patent No.: US 11,896,491 B2
(45) Date of Patent: *Feb. 13, 2024

(54) EXPANDABLE TOTAL DISC REPLACEMENT IMPLANT

(71) Applicant: Loubert S. Suddaby, Orchard Park, NY (US)

(72) Inventor: Loubert S. Suddaby, Orchard Park, NY (US)

(*) Notice: Subject to any disclaimer, the term of this patent is extended or adjusted under 35 U.S.C. 154(b) by 0 days.

This patent is subject to a terminal disclaimer.

(21) Appl. No.: 17/658,343

(22) Filed: Apr. 7, 2022

(65) Prior Publication Data

US 2023/0118386 A1    Apr. 20, 2023

Related U.S. Application Data

(63) Continuation-in-part of application No. 17/451,338, filed on Oct. 19, 2021, now Pat. No. 11,583,410.

(51) Int. Cl.
*A61F 2/44* (2006.01)
*A61F 2/30* (2006.01)

(52) U.S. Cl.
CPC .............. *A61F 2/442* (2013.01); *A61F 2/441* (2013.01); *A61F 2002/30579* (2013.01); *A61F 2002/30601* (2013.01)

(58) Field of Classification Search
CPC ........ A61F 2/441; A61F 2/442; A61F 2/4425; A61F 2/4455; A61F 2/446; A61F 2/4465; A61F 2/447; A61F 2002/30584; A61F 2002/30586; A61F 2002/30601; A61F 2002/443; A61F 2002/30555; A61F 2002/30581–30588
See application file for complete search history.

(56) References Cited

U.S. PATENT DOCUMENTS

| | | |
|---|---|---|
| 3,875,595 A | 4/1975 | Froning |
| 6,159,244 A | 12/2000 | Suddaby |
| 6,332,895 B1 | 12/2001 | Suddaby |
| 6,723,126 B1 | 4/2004 | Berry |
| 6,969,405 B2 | 11/2005 | Suddaby |
| 7,695,516 B2 | 4/2010 | Zeegers |
| 8,062,374 B2 | 11/2011 | Markworth et al. |
| 8,241,331 B2 | 8/2012 | Arnin |
| 8,257,439 B2 | 9/2012 | Zeegers |
| 8,409,287 B2 | 4/2013 | Braddock, Jr. et al. |
| 8,685,104 B2 | 4/2014 | Lee et al. |
| 8,845,641 B2 | 9/2014 | Wheeler et al. |

(Continued)

FOREIGN PATENT DOCUMENTS

WO    2009064787 A2    5/2009

*Primary Examiner* — Ellen C Hammond
*Assistant Examiner* — Anna V. Little
(74) *Attorney, Agent, or Firm* — Harter Secrest & Emery LLP; Michael Nicholas Vranjes

(57) ABSTRACT

An expandable intervertebral total disc replacement implant, including an inferior component, including a first core including a first outer surface and a first inner surface, and a first arm telescopingly engaged with the first core, a superior component, including a second core including a second outer surface and a second inner surface, and a second arm telescopingly engaged with the second core, and an expansion mechanism connected to the first core, the second core, and at least one of the first arm and the second arm.

15 Claims, 17 Drawing Sheets

(56) References Cited

U.S. PATENT DOCUMENTS

| | | |
|---|---|---|
| 8,906,101 B2 | 12/2014 | Lee et al. |
| 9,044,339 B2 | 6/2015 | Zeegers |
| 9,107,761 B2 | 8/2015 | Lee et al. |
| 9,283,087 B2 | 3/2016 | Lee et al. |
| 9,421,110 B2 | 4/2016 | Masson et al. |
| 9,566,164 B2 | 2/2017 | Zeegers |
| 9,566,165 B2 | 2/2017 | Lee et al. |
| 9,757,272 B2 | 9/2017 | Belson |
| 9,867,716 B2 | 1/2018 | Zeegers |
| 10,058,435 B2 | 8/2018 | Lee et al. |
| 10,137,005 B2 | 11/2018 | Ashleigh |
| 10,226,355 B2 | 3/2019 | Zeegers |
| 10,322,007 B2 | 6/2019 | Masson et al. |
| 10,376,378 B2 | 8/2019 | Ashleigh et al. |
| 10,433,980 B2 | 10/2019 | Ashleigh et al. |
| 10,765,532 B2 | 9/2020 | Ashleigh et al. |
| 11,007,067 B2 | 5/2021 | Masson et al. |
| 2004/0167626 A1 | 8/2004 | Geremakis et al. |
| 2004/0215342 A1* | 10/2004 | Suddaby ............... A61F 2/441 623/17.12 |
| 2004/0254644 A1* | 12/2004 | Taylor ................. A61F 2/4425 623/17.13 |
| 2005/0049590 A1 | 3/2005 | Alleyne et al. |
| 2005/0256576 A1* | 11/2005 | Moskowitz ............. A61F 2/441 606/104 |
| 2005/0261769 A1 | 11/2005 | Moskowitz et al. |
| 2007/0043440 A1 | 2/2007 | William et al. |
| 2007/0050033 A1* | 3/2007 | Reo ................. A61F 2/4425 623/17.13 |
| 2007/0191954 A1 | 8/2007 | Hansell et al. |
| 2007/0198089 A1* | 8/2007 | Moskowitz ............. A61F 2/442 623/17.11 |
| 2007/0255407 A1 | 11/2007 | Castleman et al. |
| 2007/0270968 A1* | 11/2007 | Baynham ............... A61F 2/447 623/17.11 |
| 2008/0021556 A1* | 1/2008 | Edie ..................... A61F 2/44 623/17.11 |
| 2008/0058931 A1* | 3/2008 | White ..................... A61F 2/44 623/17.11 |
| 2008/0140207 A1* | 6/2008 | Olmos ................. A61F 2/447 623/17.11 |
| 2008/0154305 A1 | 6/2008 | Foley et al. |
| 2008/0243251 A1* | 10/2008 | Stad ..................... A61F 2/442 606/63 |
| 2009/0125062 A1 | 5/2009 | Arnin |
| 2009/0270987 A1* | 10/2009 | Heinz ................. A61F 2/4465 623/17.11 |
| 2010/0063510 A1 | 3/2010 | Arlet et al. |
| 2010/0179657 A1 | 7/2010 | Greenhalgh et al. |
| 2010/0185288 A1* | 7/2010 | Carls ................. A61F 2/442 623/17.11 |
| 2010/0268338 A1* | 10/2010 | Melkent ................. A61F 2/44 623/17.11 |
| 2010/0268340 A1* | 10/2010 | Capote ................. A61F 2/44 623/17.11 |
| 2010/0280616 A1 | 11/2010 | Frasier |
| 2010/0286779 A1 | 11/2010 | Thibodeau |
| 2012/0191193 A1* | 7/2012 | Trieu ................. A61F 2/4611 623/17.16 |
| 2014/0031938 A1* | 1/2014 | Lechmann ........... A61F 2/4425 623/17.16 |
| 2014/0215342 A1* | 7/2014 | Watanabe ........... G06F 3/04842 715/732 |
| 2014/0243982 A1* | 8/2014 | Miller ................. A61F 2/447 623/17.16 |
| 2016/0166404 A1 | 6/2016 | Faulhaber |
| 2017/0172760 A1 | 6/2017 | Loebl et al. |
| 2018/0078384 A1* | 3/2018 | Suddaby ............... A61F 2/4611 |
| 2018/0318101 A1 | 11/2018 | Engstrom |
| 2018/0344476 A1* | 12/2018 | Koch ................. A61F 2/4611 |
| 2018/0368983 A1 | 12/2018 | Werner |
| 2019/0053912 A1* | 2/2019 | Suddaby ............... A61F 2/447 |
| 2019/0133784 A1 | 5/2019 | Gunn et al. |

\* cited by examiner

EXPANDABLE TOTAL DISC REPLACEMENT IMPLANT

CROSS-REFERENCE TO RELATED APPLICATIONS

This application is filed under 35 U.S.C. § 120 as a continuation-in-part of U.S. patent application Ser. No. 17/451,338, filed on Oct. 19, 2021, which reference is hereby incorporated by reference in its entirety.

FIELD

The present disclosure relates to orthopedic surgery, and more particularly to an expandable and deployable intervertebral or total disc replacement implant capable of being placed within an intervertebral disc space and expanded.

BACKGROUND

The spinal column, or backbone, is one of the most important parts of the body. It provides the main support, allowing us to stand upright, bend, and twist. As shown in FIG. 1, thirty three (33) individual bones interlock with each other to form the spinal column. The vertebrae are numbered and divided into regions. The cervical vertebrae C1-C7 form the neck, support the head and neck, and allow nodding and shaking of the head. The thoracic vertebrae T1-T12 join with the ribs to form the rib cage. The five lumbar vertebrae L1-L5 carry most of the weight of the upper body and provide a stable center of gravity when a person moves. Five vertebrae of the sacrum S and four of the coccyx C are fused. This comprises the back wall of the pelvis. Intervertebral discs are located between each of the mobile vertebra. Intervertebral discs comprise a thick outer layer with a crisscrossing fibrous structure annulus A that surrounds a soft gel-like center, the nucleus N. Discs function like shock-absorbing springs. The annulus pulls the vertebral bodies together against the elastic resistance of the gel-filled nucleus. When we bend, the nucleus acts like a ball bearing, allowing the vertebral bodies to roll over the incompressible gel. Each disc works in concert with two facet joints, forming a spinal motion segment. The biomechanical function of each pair of facet joints is to guide and limit the movement of the spinal motion segment. The surfaces of the joint are coated with cartilage that helps each joint move smoothly. Directly behind the discs, the ring-like vertebral bodies create a vertical tunnel called the spinal canal or neuro canal. The spinal cord and spinal nerves pass through the spinal canal, which protects them from injury. The spinal cord is the major column of nerve tissue that is connected to the brain and serves as an information super-highway between the brain and the body. The nerves in the spinal cord branch off to form pairs of nerve roots that travel through the small openings between the vertebrae and the intervertebral foramens.

Various medical conditions require a surgeon to repair, remove and/or replace the aforementioned discs. For example, in one surgical procedure, known as a discectomy (or diskectomy) with interbody fusion, the surgeon removes the nucleus of the disc and replaces it with an implant. As shown in FIG. 2, it may be necessary, for example, for the surgeon to remove the nucleus of the disc between the L3 and L4 vertebrae. Disc $D_{L3-L4}$ is shown in an enlarged view in FIG. 3. This figure also shows various anatomical structures of the spine, including facets F3A and F4A, facet joint FJ, spinous processes SP3 (not shown) and SP4, transverse processes TP3A and TP4A, and intervertebral foramen IF. FIG. 4 is a top view of the section of the spinal column shown in FIG. 3, with the L3 vertebra removed to expose annulus A and nucleus N of disc $D_{L3-L4}$. Neural canal NC is also shown. FIG. 5 is an anterior perspective view of the section of the spinal column shown in FIG. 4. FIG. 6 is a partial cross-sectional view of the section of the spinal column shown in FIG. 5, taken generally along line 6-6, but with vertebra L3 in place atop disc $D_{L3-L4}$.

Of all animals possessing a backbone, human beings are the only creatures who remain upright for significant periods of time. From an evolutionary standpoint, this erect posture has conferred a number of strategic benefits, not the least of which is freeing the upper limbs for purposes other than locomotion. From an anthropologic standpoint, it is also evident that this unique evolutionary adaptation is a relatively recent change, and as such has not benefitted from natural selection as much as have backbones held in a horizontal attitude. As a result, the stresses acting upon the human backbone (or "vertebral column"), are unique in many senses, and result in a variety of problems or disease states that are peculiar to the human species.

The human vertebral column is essentially a tower of bones held upright by fibrous bands called ligaments and contractile elements called muscles. There are seven bones in the neck or cervical region, twelve in the chest or thoracic region, five in the lower back or lumbar region, and five in the pelvic or sacral region, which are normally fused together to form the back part of the pelvis. This column of bones is critical for providing structural support for the entire body.

Between the vertebral bones themselves exist soft tissue structures, i.e., discs, composed of fibrous tissue and cartilage that are compressible and act as shock absorbers for sudden downward forces on the upright column. The discs allow the bones to move independently of each other, as well. The repetitive forces which act on these intervertebral discs during repetitive activities of bending, lifting, and twisting cause them to break down or degenerate over time.

Presumably, because of humans' upright posture their intervertebral discs have a high propensity to degenerate. Overt trauma or covert trauma, occurring in the course of repetitive activities, disproportionately affects the more highly mobile areas of the spine. Disruption of a disc's internal architecture leads to bulging, herniation, or protrusion of pieces of the disc and eventual disc space collapse. Resulting mechanical and even chemical irritation of surrounding neural elements (spinal cord and nerves) cause pain, attended by varying degrees of disability. In addition, loss of disc space height relaxes tension on the longitudinal spinal ligaments, thereby contributing to varying degrees of spinal movement.

The time-honored method of addressing the issues of neural irritation and instability resulting from severe disc damage has largely focused on removal of the damaged disc and fusing the adjacent vertebral elements together. Removal of the disc relieves the mechanical and chemical irritation of neural elements, while osseous union (i.e., bone knitting) solves the problem of stability.

While bony fusion restores stability and relieves pain by removing the compressive and chemical irritation caused by damaged disc fragments, it does not restore normal mobility at the damages segment. Lack of motion caused by a fusion stresses adjacent mobile segments causing them to break down prematurely.

Total disc replacement prostheses are currently implanted from an anterior approach. During implantation from an anterior approach (i.e., from the front of the body), retraction of the great blood vessels is required and greatly enhances the risk of devastating complications such as vascular tears or thrombosis. Compromising an implant size may result in too small an endplate surface area leading to subsidence and loosening the implant or to malposition thereby failing to capture the ideal center of rotation with the replacement causing abnormal stresses on surrounding ligaments and facet joints.

Thus, there is a long-felt need for an expandable and deployable intervertebral disc replacement implant capable of being placed within an intervertebral disc space and expanded.

SUMMARY

According to aspects illustrated herein, there is provided an expandable intervertebral total disc replacement implant, comprising an inferior component, including a first core comprising a first outer surface and a first inner surface, and a first arm telescopingly engaged with the first core, a superior component, including a second core comprising a second outer surface and a second inner surface, and a second arm telescopingly engaged with the second core, and an expansion mechanism connected to the first core, the second core, and at least one of the first arm and the second arm.

In some embodiments, the expansion mechanism is operatively arranged to displace the superior component with respect to the inferior component. In some embodiments, the expansion mechanism is operatively arranged to displace the at least one arm with respect to its respective core. In some embodiments, the expansion mechanism is an inflatable sac. In some embodiments, the inflatable sac is connected to the at least one of the first arm and the second arm at an outer perimeter of the inflatable sac. In some embodiments, the inflatable sac is connected to the first arm and the second arm. In some embodiments, the expansion mechanism is connected to the first inner surface and the second inner surface. In some embodiments, the first core comprises a first radial extending aperture and the first arm is engaged with the first radial extending aperture. In some embodiments, at least one of the first inner surface and the second inner surface comprises a recess, and the expansion mechanism is slidingly engaged with the recess.

In some embodiments, the first arm comprises a first protrusion telescopingly engaged with the first core, a third outer surface, and a third inner surface, wherein in a fully collapsed state the third outer surface is aligned with the first outer surface to form a first continuous outer surface. In some embodiments, the second arm comprises a second protrusion telescopingly engaged with the second core, a fourth outer surface, and a fourth inner surface, wherein in the fully collapsed state the fourth outer surface is aligned with the second outer surface to form a second continuous outer surface. In some embodiments, the superior component is axially displaceable relative to the inferior component, the first arm is radially displaceable with respect to the first core, and the second arm is radially displaceable with respect to the second core. In some embodiments, at least one of the inferior component and the superior component are pivotable with respect to the expansion mechanism.

According to aspects illustrated herein, there is provided an expandable intervertebral total disc replacement implant, comprising an inferior component, including a first core comprising a first outer surface and a first inner surface, and a superior component, including a second core comprising a second outer surface and a second inner surface, an arm telescopingly engaged with at least one of the first core and the second core, and an inflatable sac connected to the first core, the second core, and the arm.

In some embodiments, the inflatable sac is operatively arranged to displace the superior component with respect to the inferior component, and the arm with respect to its respective core. In some embodiments, the inflatable sac is slidably connected to the first inner surface and the second inner surface. In some embodiments, the first core comprises a radial extending aperture and the arm is engaged with the radial extending aperture. In some embodiments, at least one of the first inner surface and the second inner surface comprises a recess, and the expansion mechanism is pivotably engaged with the recess. In some embodiments, the superior component is axially displaceable relative to the inferior component, and the arm is radially displaceable with respect to the at least one of the first core and the second core. In some embodiments, at least one of the inferior component and the superior component are pivotable with respect to the expansion mechanism.

According to aspects illustrated herein, there is provided an expandable intervertebral total disc replacement implant, comprising an inferior component, including a first core comprising a first outer surface and a first inner surface, and a first plurality of arms telescopingly engaged with the first core, a superior component, including a second core comprising a second outer surface and a second inner surface, and a second plurality of arms telescopingly engaged with the second core, and an expansion mechanism connected to the first inner surface and the second inner surface, the expansion mechanism operatively arranged to displace the superior component with respect to the inferior component.

In some embodiments, the expansion mechanism is an inflatable sac. In some embodiments, the expansion mechanism comprises a first component including first plurality of teeth, and a second component including a second plurality of teeth, wherein the second plurality of teeth engage the first plurality of teeth to prevent the superior component from displacing toward the inferior component. In some embodiments, the expansion mechanism is a screw jack. In some embodiments, the first core comprises a first plurality of radial extending apertures and the first plurality of arms are engaged with the first plurality of radial extending apertures. In some embodiments, each of the first plurality of radial extending apertures is arranged between and spaced apart from the first outer surface and the first inner surface. In some embodiments, at least one of the first inner surface and the second inner surface comprises a recess, and the expansion mechanism is engaged with the recess.

In some embodiments, each arm of the first plurality of arms comprises a first protrusion telescopingly engaged with the first core, a third outer surface, and a third inner surface, wherein in a fully collapsed state the third outer surface is aligned with the first outer surface to form a first continuous outer surface. In some embodiments, each arm of the second plurality of arms comprises a second protrusion telescopingly engaged with the second core, a fourth outer surface, and a fourth inner surface, wherein in the fully collapsed state the fourth outer surface is aligned with the second outer surface to form a second continuous outer surface.

In some embodiments, in the fully collapsed state the fourth inner surface abuts against the third inner surface. In some embodiments, the superior component is axially displaceable relative to the inferior component, the first plurality of arms are radially displaceable with respect to the first core, and the second plurality of arms are radially displaceable with respect to the second core. In some embodiments, at least one of the inferior component and the superior component are pivotable with respect to the expansion mechanism. In some embodiments, the first plurality of arms are displaceable with respect to each other and the second plurality of arms are displaceable with respect to each other.

According to aspects illustrated herein, there is provided an expandable intervertebral total disc replacement implant, comprising an inferior component, including a first core comprising a first outer surface, a first inner surface, and a first plurality of apertures arranged between the first outer surface and the first inner surface, and a first plurality of arms slidingly engaged with the first plurality of apertures, a superior component, including a second core comprising a second outer surface, a second inner surface, and a second plurality of apertures arranged between the second outer surface and the second inner surface, and a second plurality of arms slidingly engaged with the second plurality of apertures, and an expansion mechanism connected to the first inner surface and the second inner surface, the expansion mechanism operatively arranged to axially displace the superior component with respect to the inferior component.

In some embodiments, the expansion mechanism is an inflatable balloon. In some embodiments, the first plurality of arms are radially displaceable with respect to the first core, and the second plurality of arms are radially displaceable with respect to the second core. In some embodiments, at least one of the inferior component and the superior component are pivotable with respect to the expansion mechanism. In some embodiments, the first plurality of arms are displaceable with respect to each other and the second plurality of arms are displaceable with respect to each other. In some embodiments, each of the first plurality of radial extending apertures is spaced apart from the first outer surface and the first inner surface. In some embodiments, the first inner surface comprises a first recess, the second inner surface comprises a second recess, and the expansion mechanism is engaged with the first recess and the second recess.

According to aspects illustrated herein, there is provided a system relating to orthopedic surgery, and more particularly, to a prosthetic intervertebral disc replacement system which can be implanted into a suitably prepared intervertebral disc space via minimally invasive surgical techniques to provide for and restore substantial normalcy of movement.

According to aspects illustrated herein, there is provided a system including adjustable endplates and an adjustable mobile core such that anatomic variants can be more precisely accommodated and so ligaments can be restored to normal tensions that occurred prior to the onset of degeneration. The mobile adjustment core can be unconstrained, constrained, or semi-constrained to better approximate a normal axis of rotation.

The system comprises artificial endplates having slidable arms extending from a center axis cup. These arms are mechanically deployable and adjustable such that they can be positioned well under the cortical rim of the vertebrae to mitigate the tendency of the prosthesis to subside in the softer central vertebral bone. Adjustment of the arms situated in an anterior posterior attitude also permits optimization of the center of rotation of the device which generally lies a third of the distance anterior to the posterior cortical limit.

Because the arms are mechanically deployable after implantation of the endplates, a much smaller disc opening can be made to enucleate the disc nucleus so that surrounding ligaments can be maximally preserved. Since it is largely the ligaments and facet joints that determine normal disc motion, preserving as much of the surrounding ligaments as possible would seem prudent.

At the center of the endplates is a cup or depression that can accommodate the central core of the device in a constrained, unconstrained, semi-constrained, or other fashion. This can be varied as well whereby the superior end plate constrains the core and the inferior endplate does not, and so forth.

The wear surfaces between the endplates and the core can be metal, ceramic, plastic, or combinations thereof.

In some embodiments, the system has an adjustable core which can permit incremental changes in height to optimally restore ligamentous tautness and consequentially normal ranges of motion. While the core can be adjusted mechanically (ratcheting member, screw jack, etc.), in some embodiments the core is expanded hydraulically such that pressure can be monitored while expansion occurs. By measuring pressure and observing facet distraction under fluoroscopy, excessive forces that might damage ligaments or encourage endplate fracture and subsidence are avoided.

In some embodiments, therefore, the system comprises a distensible sac or chamber which can first be inflated with saline or contrast to observe placement of the in situ configured device, observe disc height restoration and facet distraction prior to permanent implantation. Once the pressure and volume of the injectable core material is known it is removed and a similar volume of hardenable liquid polymer is injected to form a long-term stable construct with optimally placed endplates, a customized center of rotation, and a patient specific height pertaining to the disc being replaced. In some embodiments, the hardenable material comprises polymethyl methacrylate (PMMA) or polyurethane if a degree of compressibility is desired to mitigate against axial shock loads. In the case of polyurethane or other viscoelastic polymers, a prefabricated central core could be inserted with the disc complex applied to the disc space in a compressed state allowed to expand in situ. In some embodiments, the adjustable endplates comprise metal such as titanium or nitinol, polyether ether ketone (PEEK) or similar plastics or ceramic. The corresponding and mating wear surface of the core and the endplates could be ultra-high-molecular-weight polyethylene (UHMWPE), metal, ceramic, or other biocompatible materials.

Ultimately, what is achieved by the system is an infinitely adjustable endplate/core prosthetic total disc replacement device that can be inserted via minimally invasive techniques and optimized dimensionally in situ to provide a customized patient specific disc replacement. By inserting the device in a collapsed state and expanding it in situ, much of the surrounding ligamentous structure can be preserved. This is important insofar that it is the surrounding ligaments that determine the general limits of normal motion while the disc serves more as a mobile fulcrum around which motion occurs.

In some embodiments, the endplate arms comprise nitinol or plastic polymers capable of slight but sufficient flex to better conform to variations in endplate curvature. These endplate surfaces abutting the boney surfaces shall be coated, contain, or manufactured with porous materials that favor and allow bone ingrowth to assist in anchoring the device. Spikes or small ridges could also be employed on or at the interface with the bone when the endplate is pushed against the bone upon expansion of the core.

The implant of the present disclosure allows for an insertion opening that is significantly smaller than other implants thus preserving more of the support ligaments. In some embodiments, the expansion mechanism of the implant comprises a ratcheting mechanism expandable core. In some embodiments, the expansion mechanism of the implant comprises an inflatable core including an inflation port. The inflatable core can be inflated using hardenable polymers like acrylic (PMMA) or other suitable viscoelastic polymers (e.g., polyurethane). In some embodiments, the expansion mechanism of the implant comprises a screw jack and/or a worm drive. In some embodiments, the expansion mechanism of the implant comprises a scissor jack and a screw that engages the scissor jack. As is known in the art of scissor jacks, as the screw is turned in a first direction, the scissor jack increases in height, and as the screw is turned in a second direction, opposite the first direction, the scissor jack decreases in height.

The implant comprises extendable arms or endplate wings which slidingly and/or telescopingly engage a central core of the implant. In some embodiments, the central core of the implant is 6-7 mm in diameter. In some embodiments, in a fully collapsed state, the diameter of the entire implant is between 10 and 14 mm. In some embodiments, in a fully collapsed state, the diameter of the implant in a first direction is 10 mm and the diameter of the implant in a second direction is 14 mm. In some embodiments, in a fully expanded state, the diameter of the entire implant is 16 mm. These approximations are estimates for a cervical disc replacement whereas lumbar disc replacements would be expected to be larger and fully expanded diameters may be 35-45 mm. In either case the expanded size should be chosen to allow the implant to extend beyond the inner portion of the apophysis ring at the periphery of the endplate to prevent subsidence.

These and other objects, features, and advantages of the present disclosure will become readily apparent upon a review of the following detailed description of the disclosure, in view of the drawings and appended claims.

BRIEF DESCRIPTION OF THE DRAWINGS

Various embodiments are disclosed, by way of example only, with reference to the accompanying schematic drawings in which corresponding reference symbols indicate corresponding parts, in which.

DETAILED DESCRIPTION

Figure 1:
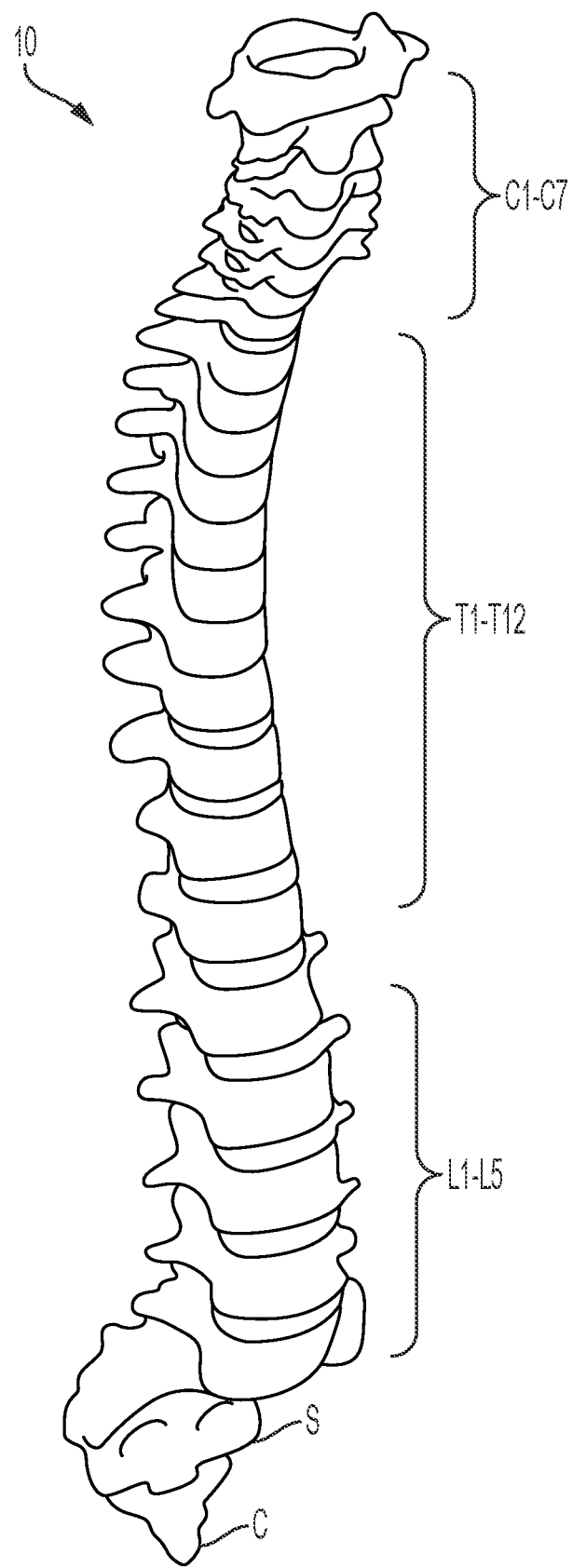
FIG. 1 is an anterior perspective view of a spinal column.
Figure 2:
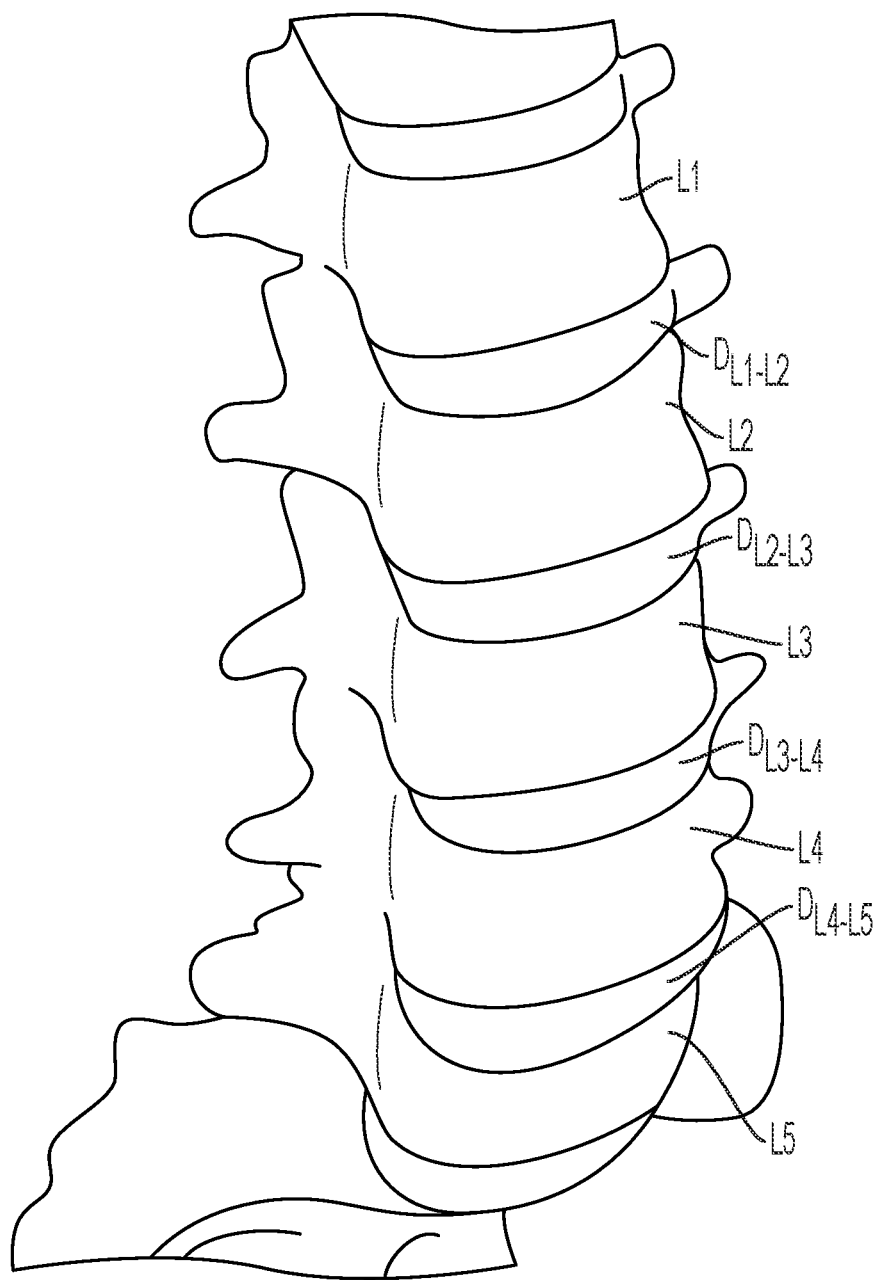
FIG. 2 is an anterior perspective view of the lumbar section of the spinal column shown in FIG. 1.
Figure 3:
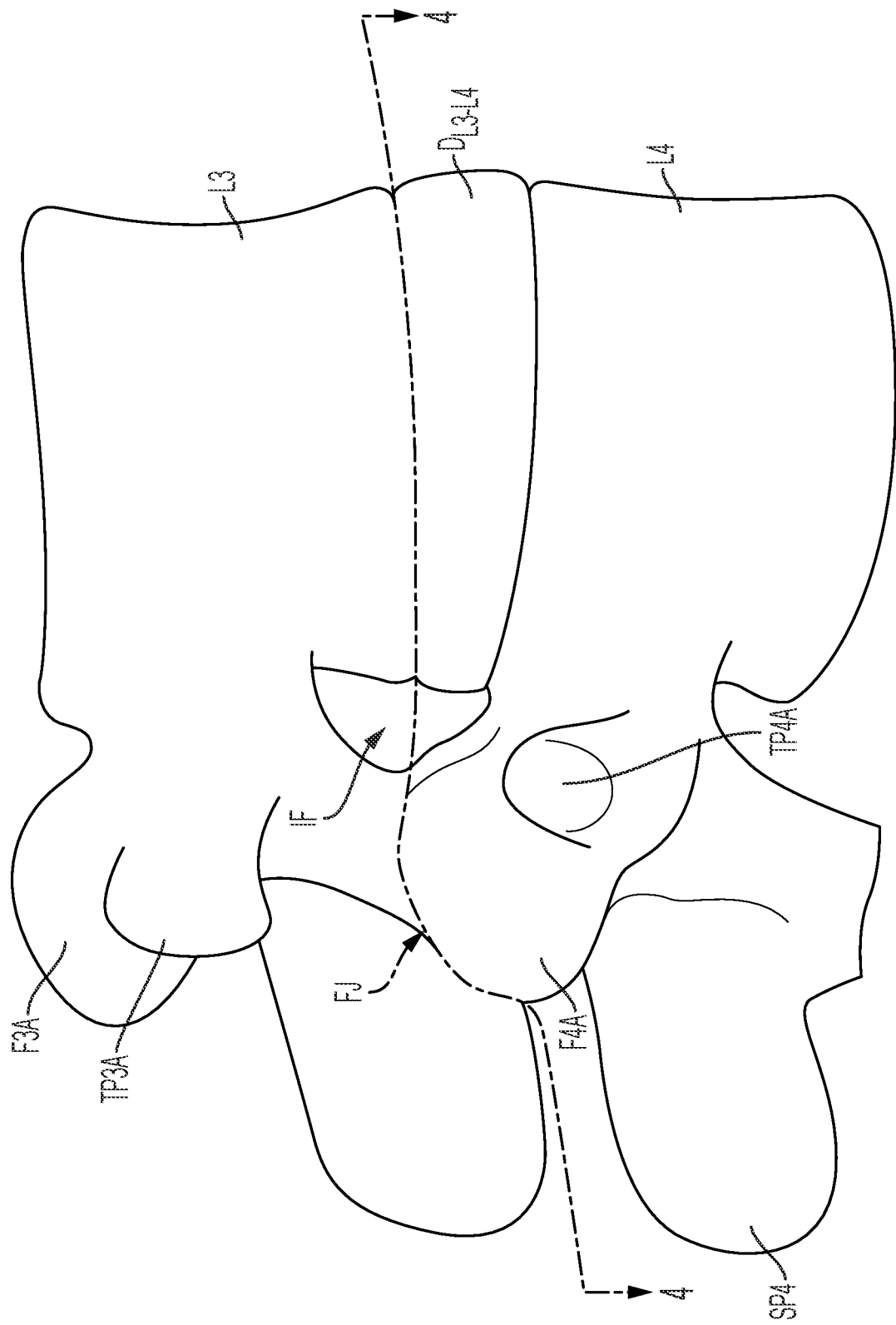
FIG. 3 is a lateral perspective view of two vertebrae, a disc, and related spinal anatomy.
Figure 4:
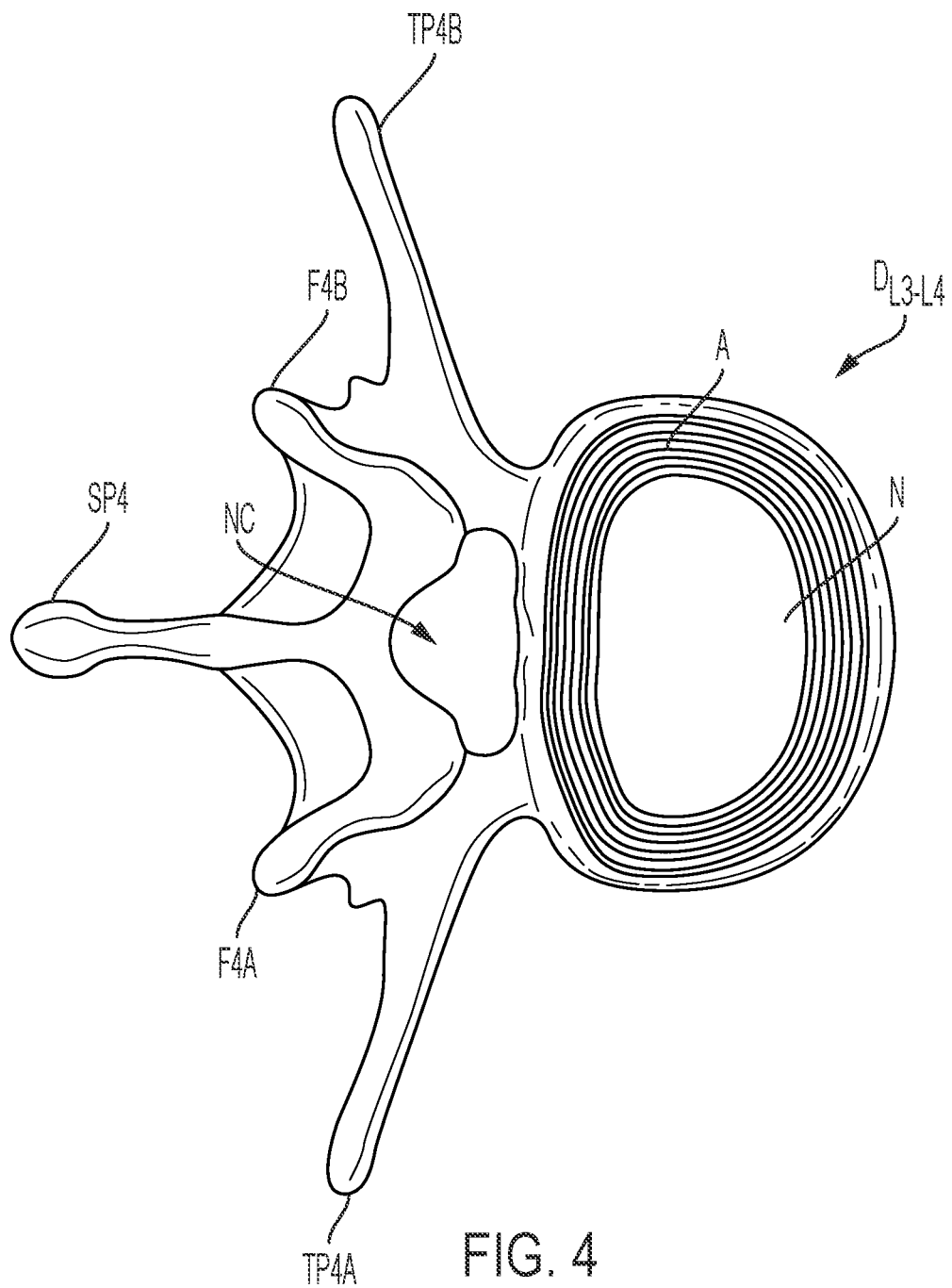
FIG. 4 is a top view of a section of the spinal column, taken generally along line 4-4 in FIG. 3.
Figure 5:
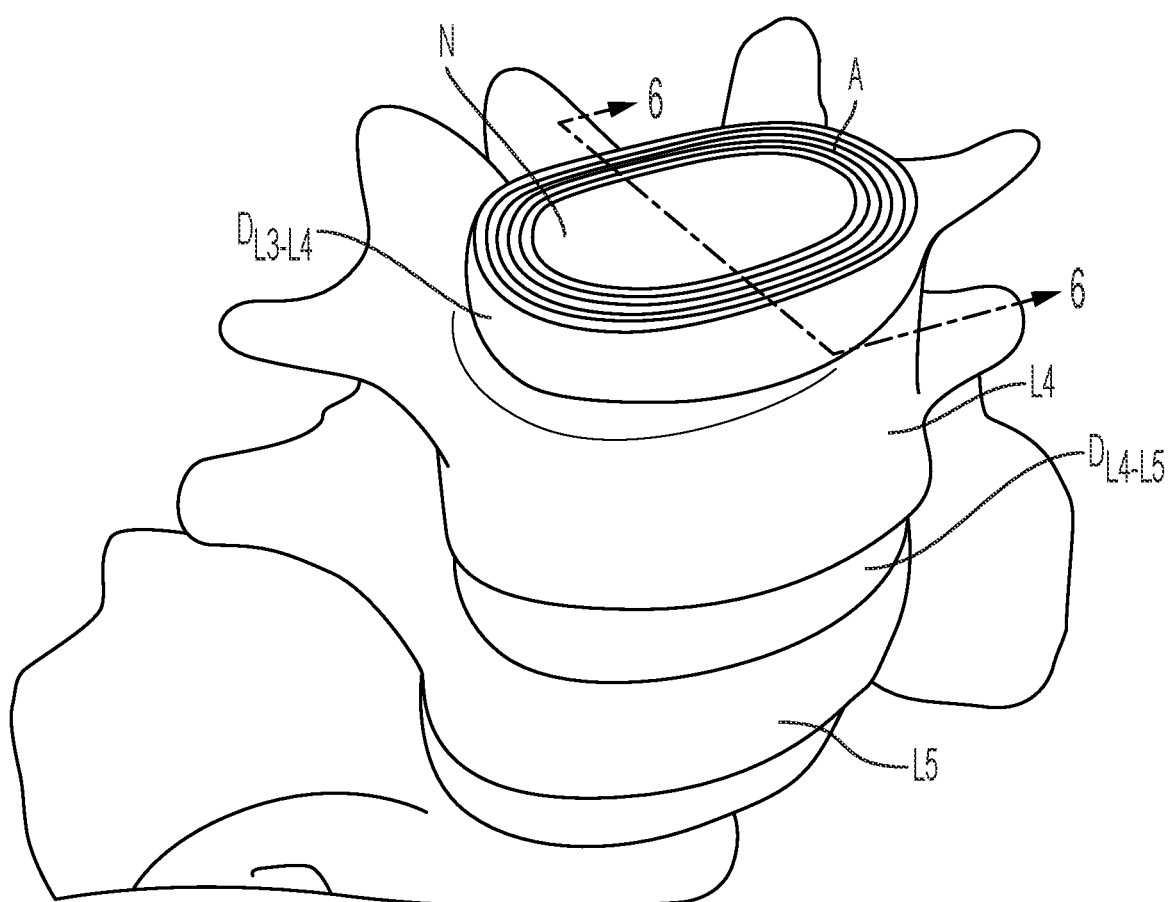
FIG. 5 is an enlarged anterior perspective view of the spinal column shown in FIG. 2, except with the top vertebra and all other structure above the top vertebra removed.
Figure 6:
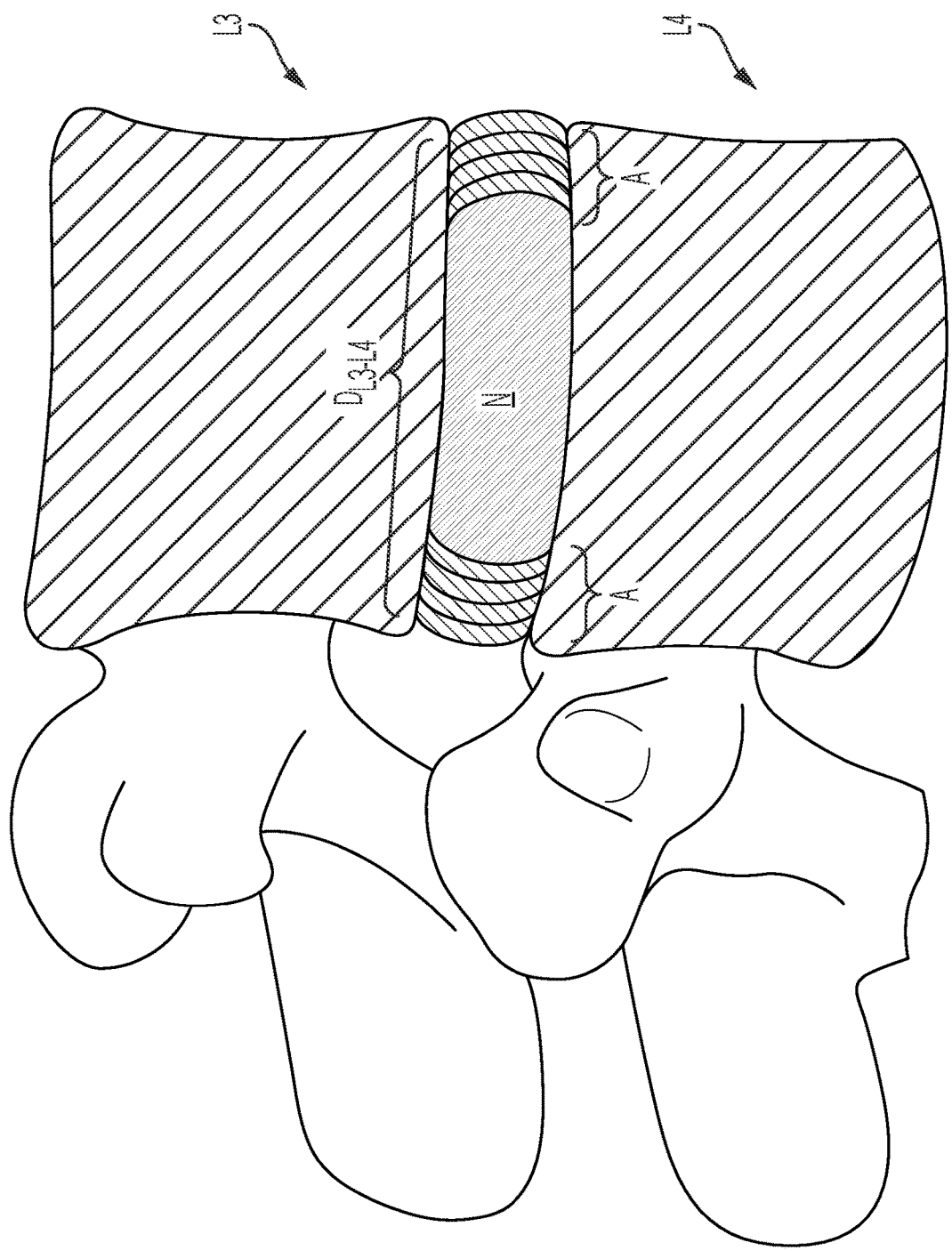
FIG. 6 is a partial cross-sectional view of the top and bottom vertebrae and disc, taken generally along line 6-6 in FIG. 5.

At the outset, it should be appreciated that like drawing numbers on different drawing views identify identical, or functionally similar, structural elements. It is to be understood that the claims are not limited to the disclosed aspects.

Furthermore, it is understood that this disclosure is not limited to the particular methodology, materials and modifications described and as such may, of course, vary. It is also understood that the terminology used herein is for the purpose of describing particular aspects only, and is not intended to limit the scope of the claims.

Unless defined otherwise, all technical and scientific terms used herein have the same meaning as commonly understood to one of ordinary skill in the art to which this disclosure pertains. It should be understood that any methods, devices or materials similar or equivalent to those described herein can be used in the practice or testing of the example embodiments. The assembly of the present disclosure could be driven by hydraulics, electronics, pneumatics, and/or springs.

It should be appreciated that the term "substantially" is synonymous with terms such as "nearly," "very nearly," "about," "approximately," "around," "bordering on," "close to," "essentially," "in the neighborhood of," "in the vicinity of," etc., and such terms may be used interchangeably as appearing in the specification and claims. It should be appreciated that the term "proximate" is synonymous with terms such as "nearby," "close," "adjacent," "neighboring," "immediate," "adjoining," etc., and such terms may be used interchangeably as appearing in the specification and claims. The term "approximately" is intended to mean values within ten percent of the specified value.

It should be understood that use of "or" in the present application is with respect to a "non-exclusive" arrangement, unless stated otherwise. For example, when saying that "item x is A or B," it is understood that this can mean one of the following: (1) item x is only one or the other of A and B; (2) item x is both A and B. Alternately stated, the word "or" is not used to define an "exclusive or" arrangement. For example, an "exclusive or" arrangement for the statement "item x is A or B" would require that x can be only one of A and B. Furthermore, as used herein, "and/or" is intended to mean a grammatical conjunction used to indicate that one or more of the elements or conditions recited may be included or occur. For example, a device comprising a first element, a second element and/or a third element, is intended to be construed as any one of the following structural arrangements: a device comprising a first element; a device comprising a second element; a device comprising a third element; a device comprising a first element and a second element; a device comprising a first element and a third element; a device comprising a first element, a second element and a third element; or, a device comprising a second element and a third element.

Moreover, as used herein, the phrases "comprises at least one of" and "comprising at least one of" in combination with a system or element is intended to mean that the system or element includes one or more of the elements listed after the phrase. For example, a device comprising at least one of: a first element; a second element; and, a third element, is intended to be construed as any one of the following structural arrangements: a device comprising a first element; a device comprising a second element; a device comprising a third element; a device comprising a first element and a second element; a device comprising a first element and a third element; a device comprising a first element, a second element and a third element; or, a device comprising a second element and a third element. A similar interpretation is intended when the phrase "used in at least one of:" is used herein. Furthermore, as used herein, "and/or" is intended to mean a grammatical conjunction used to indicate that one or more of the elements or conditions recited may be included or occur. For example, a device comprising a first element, a second element and/or a third element, is intended to be construed as any one of the following structural arrangements: a device comprising a first element; a device comprising a second element; a device comprising a third element; a device comprising a first element and a second element; a device comprising a first element and a third element; a device comprising a first element, a second element and a third element; or, a device comprising a second element and a third element.

By "non-rotatably connected" elements, we mean that: the elements are connected so that whenever one of the elements rotate, all the elements rotate; and, relative rotation between the elements is not possible. Radial and/or axial movement of non-rotatably connected elements with respect to each other is possible, but not required. By "rotatably connected" elements, we mean that: the elements are rotatable with respect to each other; and, whenever one element is displaced radially and/or axially, all the elements are displaced radially and/or axially.

Adverting now to the figures, and as described previously, FIGS. 1-6 depict various parts and sections of spinal anatomy.

Figure 7A:
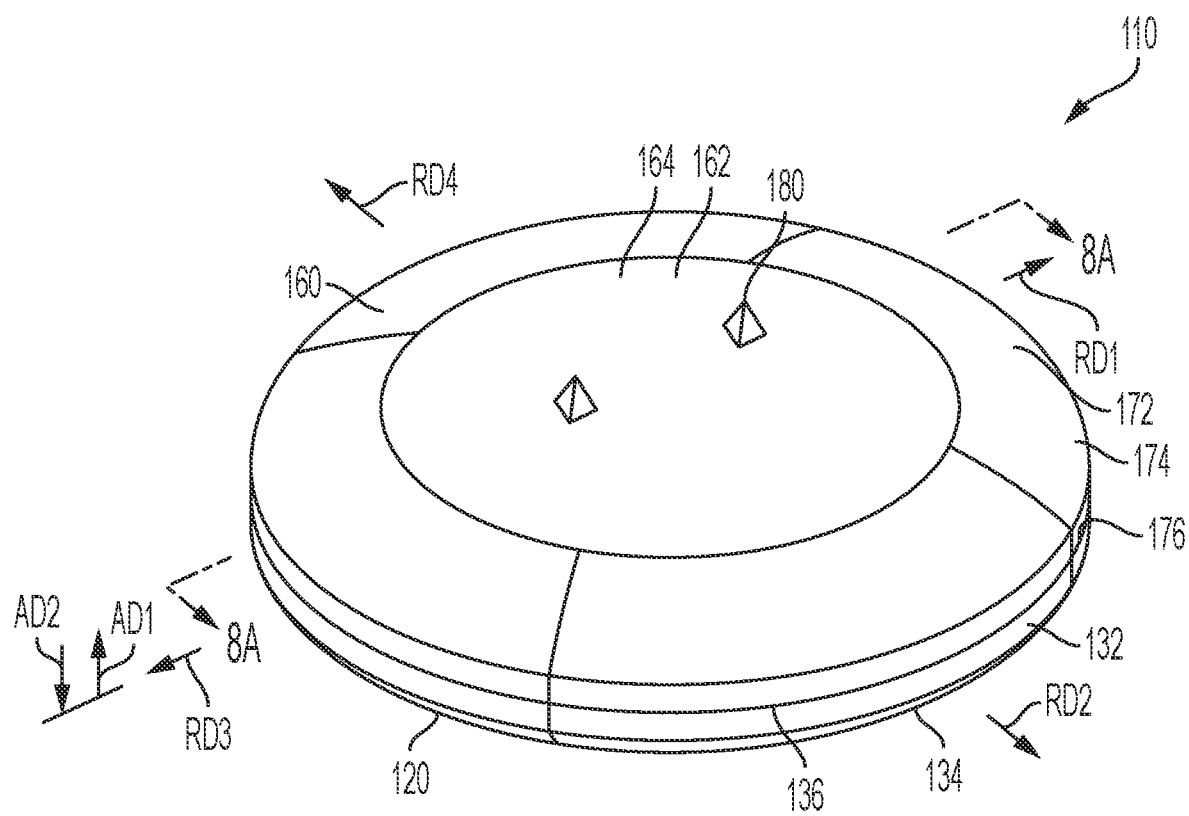
FIG. 7A is a front perspective view of an expandable total disc replacement implant, in a collapsed state.
Figure 7B:
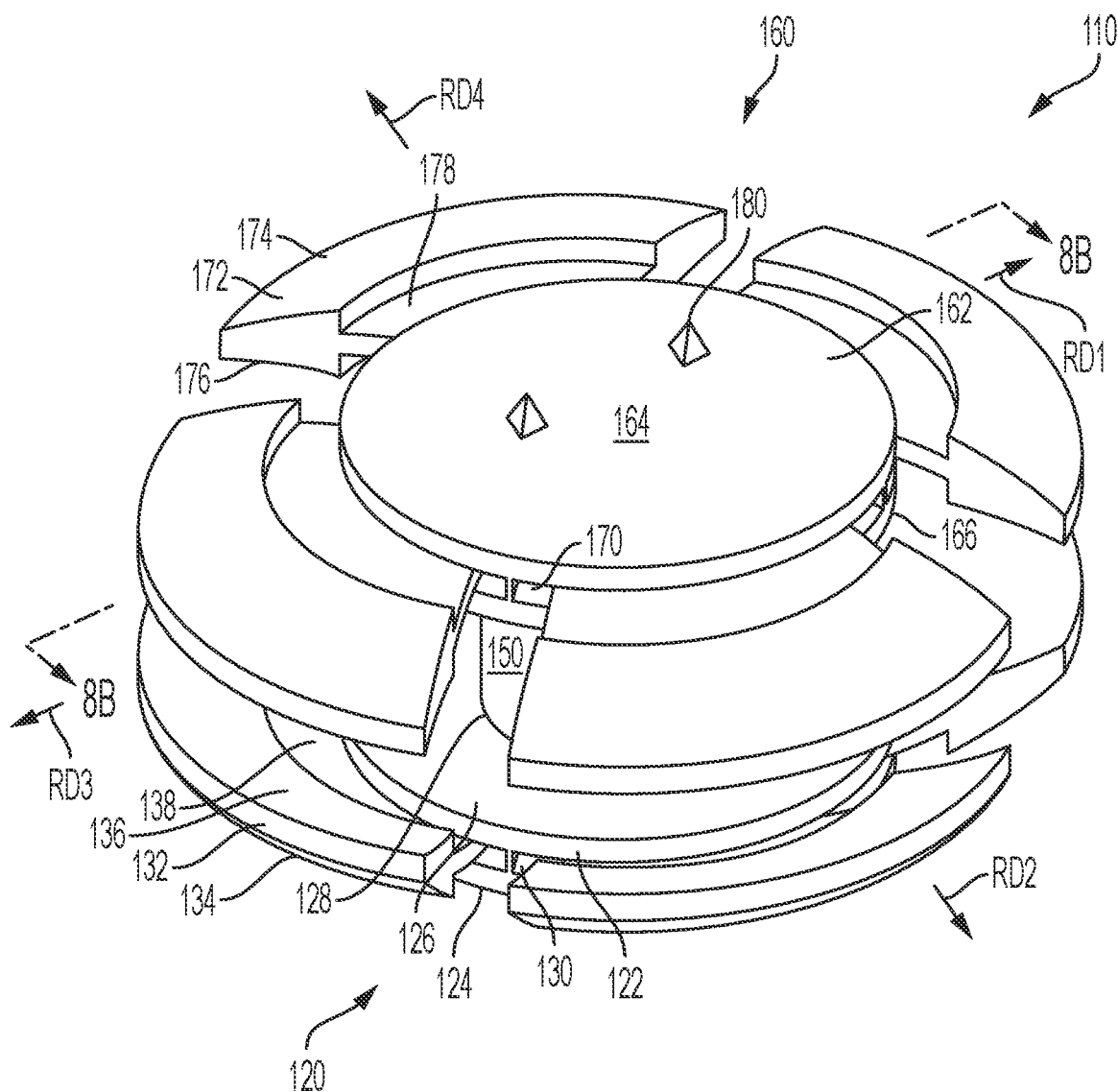
FIG. 7B is a front perspective view of the expandable total disc replacement implant shown in FIG. 7A, in an expanded state.
Figure 8A:
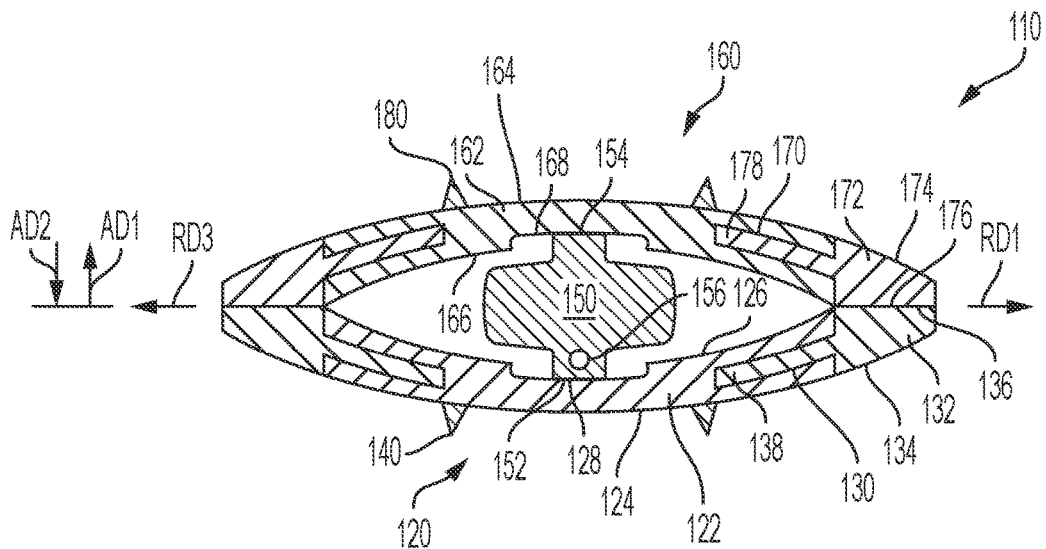
FIG. 8A is a cross-sectional view of the expandable total disc replacement implant taken generally along line 8A-8A in FIG. 7A.
Figure 8B:
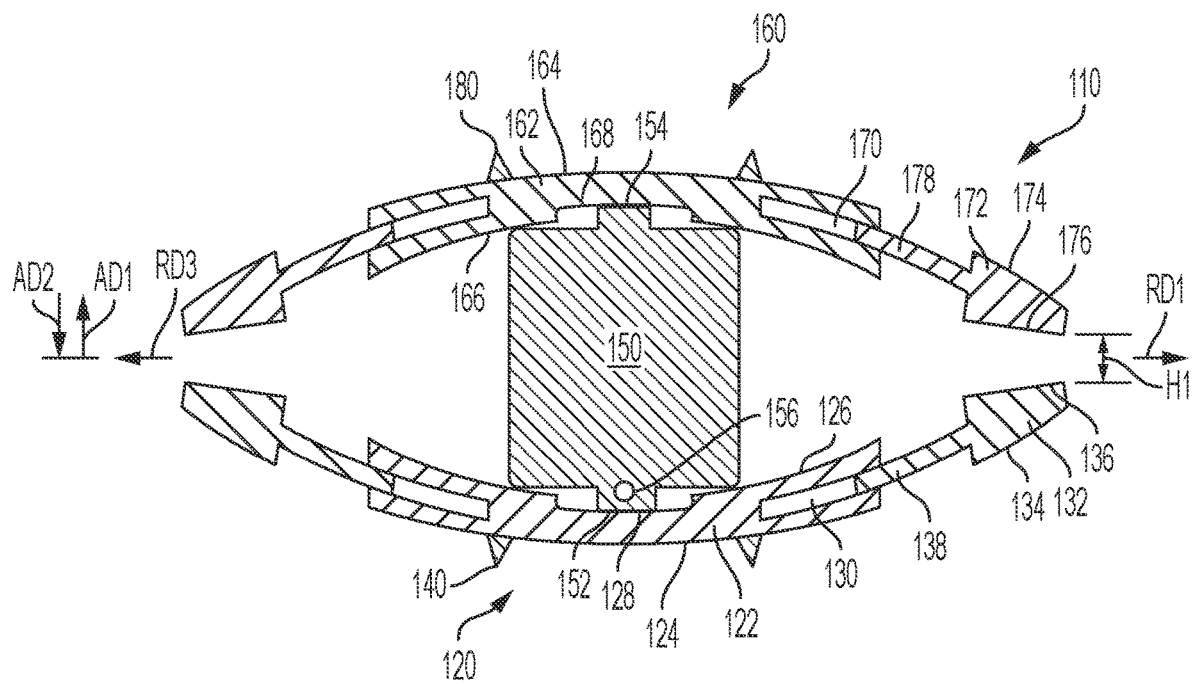
FIG. 8B is a cross-sectional view of the expandable total disc replacement implant taken generally along line 8B-8B in FIG. 7B.

FIG. 7A is a front perspective view of expandable total disc replacement implant 110, in a collapsed state. FIG. 7B is a front perspective view of expandable total disc replacement implant 110, in an expanded state. FIG. 8A is a cross-sectional view of expandable total disc replacement implant 110 taken generally along line 8A-8A in FIG. 7A. FIG. 8B is a cross-sectional view of expandable total disc replacement 110 implant taken generally along line 8B-8B in FIG. 7B. Expandable total disc replacement implant 110, or implant 110, generally comprises inferior component 120, superior component 160, and an expansion mechanism, for example, expansion mechanism 150, 250, 350. The following description should be read in view of FIGS. 7A-8B.

Inferior component 120 comprises core 122 and one or more arms 132 slidingly and/or telescopingly engaged with core 122. In some embodiments, and as best shown in FIGS. 7A-B, inferior component 120 comprises four arms 132. Core 122 comprises outer surface 124, inner surface 126, recess 128, and one or more apertures 130. Outer surface 124 generally faces radially outward and is operatively arranged to engage an adjacent vertebra (see FIG. 11). Inner surface 126 generally faces radially inward, or toward superior component 160. Inner surface 126 comprises recess 128 operatively arranged to engage expansion mechanism 150. The engagement of expansion mechanism 150 with recess 128 limits radial displacement of expansion mechanism 150 with respect to inferior component 120. In some embodiments, expansion mechanism 150 is translationally connected to inferior component 120 such that it slides within recess 128. Such arrangement allows translational movement between inferior component 120 and superior component 160. Apertures 130 are arranged radially within core 122. Specifically, apertures 130 extend from an outermost perimeter of core 122 radially inward. In some embodiments, and as shown, apertures 130 reside between and spaced apart from outer surface 124 and inner surface 126. Apertures 130 allow arms 132 to be telescopingly and/or slidingly engaged with core 122. In some embodiments, core 122 comprises four apertures 130 to engage with four arms 132.

Each of arms 132 comprises outer surface 134, inner surface 136, and protrusion 138. Outer surface 134 generally faces radially outward and is operatively arranged to engage with an adjacent vertebra (see FIG. 11). In some embodiments, and as shown in FIG. 8A, in the fully collapsed state outer surface 134 is aligned with outer surface 124 so as to create a smooth continuous outer surface of inferior component 120. Inner surface 136 generally faces radially inward or toward superior component 160. In some embodiments, and as shown in FIG. 8A, in the fully collapsed state, inner surface 136 engages and/or abuts against inner surface 176 of arms 172 (of superior component 160). The engagement of surfaces 136 and 176 and the alignment of surfaces 134 and 124, in the fully collapsed state, prevent ingress of material into implant 110 during insertion and also facilitates easier implantation by providing a smooth and continuous outer implant surface. Protrusion 138 is a generally radially extending element that engages aperture 130. In some embodiments, and as shown, protrusion is arranged between and spaced apart from outer surface 134 and inner surface 136. The engagement of protrusion 138 and aperture 130 creates the telescoping and/or sliding connection between arm 132 and core 122, which allows inferior component 120 to be expanded radially in a plurality of directions, as will be described in greater detail below.

In some embodiments, core 122 and/or arms 132 are flexible or elastically deformable which allows inferior component 120 to form to the adjacent vertebra for optimal engagement therewith. In some embodiments, outer surface 124 and/or outer surface 134 comprises one or more projections, for example projections 140, operatively arranged to fixedly secure inferior component 120 to the adjacent vertebra.

Superior component 160 comprises core 162 and one or more arms 172 slidingly and/or telescopingly engaged with core 162. In some embodiments, and as best shown in FIGS. 7A-B, superior component 160 comprises four arms 172. Core 162 comprises outer surface 164, inner surface 166, recess 168, and one or more apertures 170. Outer surface 164 generally faces radially outward and is operatively arranged to engage an adjacent vertebra (see FIG. 11). Inner surface 166 generally faces radially inward, or toward inferior component 120. Inner surface 166 comprises recess 168 operatively arranged to engage expansion mechanism 150. The engagement of expansion mechanism 150 with recess 168 limits radial displacement of expansion mechanism 150 with respect to superior component 160. In some embodiments, expansion mechanism 150 is translationally connected to superior component 160 such that it slides within recess 168. Such arrangement allows translational movement between superior component 160 and inferior component 120. Apertures 170 are arranged radially within core 162. Specifically, apertures 170 extend from an outermost perimeter of core 162 radially inward. In some embodiments, and as shown, apertures 170 reside between and spaced apart from outer surface 164 and inner surface 166. Apertures 170 allow arms 172 to be telescopingly and/or slidingly engaged with core 162. In some embodiments, core 162 comprises four apertures 170 to engage with four arms 172.

Each of arms 172 comprises outer surface 174, inner surface 176, and protrusion 178. Outer surface 174 generally faces radially outward and is operatively arranged to engage with an adjacent vertebra (see FIG. 11). In some embodiments, and as shown in FIG. 8A, in the fully collapsed state outer surface 174 is aligned with outer surface 164 so as to create a smooth continuous outer surface of superior component 160. Inner surface 176 generally faces radially inward or toward inferior component 120. In some embodiments, and as shown in FIG. 8A, in the fully collapsed state, inner surface 176 engages and/or abuts against inner surface 136 of arms 132 (of inferior component 120). The engagement of surfaces 176 and 166 and the alignment of surfaces 174 and 164, in the fully collapsed state, prevent ingress of material into implant 110 during insertion and also facilitates easier implantation by providing a smooth and continuous outer implant surface. Protrusion 178 is a generally radially extending element that engages aperture 170. In some embodiments, and as shown, protrusion is arranged between and spaced apart from outer surface 174 and inner surface 176. The engagement of protrusion 178 and aperture 170 creates the telescoping and/or sliding connection between arm 172 and core 162, which allows superior component 160 to be expanded radially in a plurality of directions, as will be described in greater detail below.

In some embodiments, core 162 and/or arms 172 are flexible or elastically deformable which allows superior component 160 to form to the adjacent vertebra for optimal engagement therewith. In some embodiments, outer surface 164 and/or outer surface 174 comprises one or more projections, for example projections 180, operatively arranged to fixedly secure superior component 160 to the adjacent vertebra.

Expansion mechanism or inflatable balloon or inflatable sac 150 is generally an inflatable device operatively arranged to be filled with material to displace superior component 160 with respect to inferior component 120, or vice versa. In some embodiments, inflatable sac 150 comprises an elastomer, such as rubber. In some embodiments, inflatable sac 150 comprises a nonelastic material. Inflatable sac 150 comprises first end 152, second end 154, and port 156. First end 152 is operatively arranged to engage inner surface 126, specifically recess 128, of inferior component 120 and end 154 is operatively arranged to engage inner surface 166, specifically recess 168, of superior component 160. In some embodiments, end 152 is pivotably connected to inferior component 120 and/or end 154 is pivotably connected to superior component 160. Such pivotable connection allows general movement and flexion between inferior component 120 and superior component 160, mimicking the normal movement between vertebrae via a disc. Additionally, the elastic properties of cores 122 and 162 and arms 132 and 172 allow further natural movement between vertebrae. In some embodiments, end 152 is fixedly secured to inferior component 120 and/or end 154 is fixedly secured to superior component 160. Material, such as a hardenable polymer, acrylic, PMMA, a viscoelastic polymer, polyurethane, or any other suitable material, is injected into inflatable sac 150 through port 156. As material is injected into inflatable sac 150, inflatable sac 150 expands and superior component 160 is displaced away from inferior component 120. As material is removed from inflatable sac 150, inflatable sac 150 contracts and superior component 160 is capable of displacing toward inferior component 120.

As previously described, in the fully collapsed state, as best shown in FIG. 8A, surfaces 176 engage and/or abut against surfaces 136. It should be appreciated, that in some embodiments, a gap or aperture is arranged in implant 110 such that the expansion mechanism therein is accessible in the fully collapsed state. For example, port 156 would be accessible in the fully collapsed state such that implant 110 can be expanded. In the expanded state, wherein superior component 160 is displaced in axial direction AD1 with respect to inferior component 120, as best shown in FIG. 8B, surfaces 176 are separated from surfaces 136 by height H1. This expansion (i.e., in axial direction AD1) is referred to herein as axial expansion.

Implant 110 is also capable of radial expansion, for example, in radial directions RD1-4. As best shown in FIGS. 7B and 8B, arms 132 and arms 172 can be displaced radially with respect to cores 122 and 162, respectively. For example, one of arms 132 and one of arms 172 can be displaced in radial direction RD1 with respect to cores 122 and 162, respectively, one of arms 132 and one of arms 172 can be displaced in radial direction RD3, opposite radial direction RD1, with respect to cores 122 and 162, respectively, one of arms 132 and one of arms 172 can be displaced in radial direction RD2 with respect to cores 122 and 162, respectively, and one of arms 132 and one of arms 172 can be displaced in radial direction RD4, opposite radial direction RD2, with respect to cores 122 and 162, respectively. In some embodiments, radial direction RD2 is arranged perpendicular to radial direction RD1. It should be appreciated that each of arms 132 and 172 are displaceable with respect to each other, allowing for a completely customizable radial expansion. Such customizable radial expansion allows implant 110 to be formed to the exact shape of the patient's vertebra. For example, a patient may have vertebra L4 that is larger than vertebra L3, and thus arms 172 of superior component 160 should be radially expanded less than arms 132 of inferior component 120.

Figure 9:
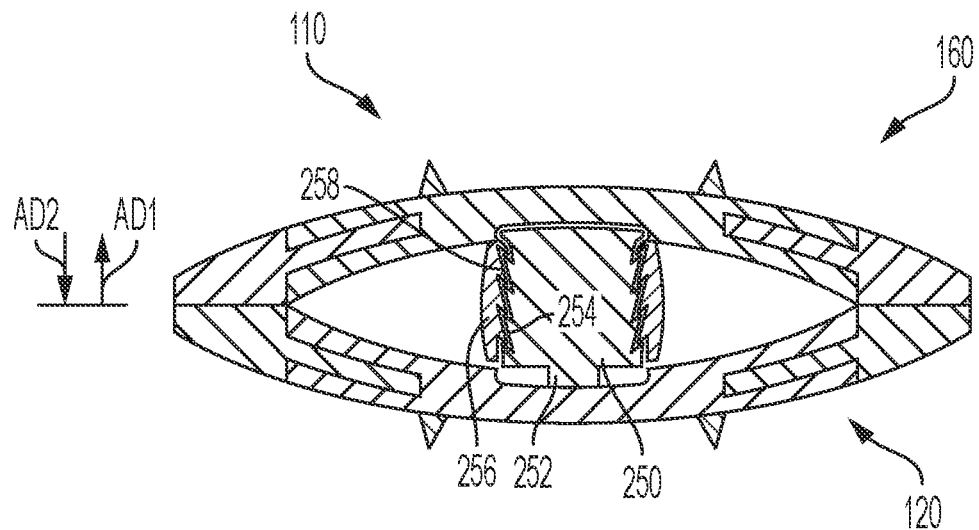
FIG. 9 is a cross-sectional view of the expandable total disc replacement implant taken generally along line 8A-8A in FIG. 7A.

FIG. 9 is a cross-sectional view of implant 110 taken generally along line 8A-8A in FIG. 7A. FIG. 9 shows expansion mechanism or ratcheting expansion mechanism 250. Ratcheting expansion mechanism 250 comprises first section 252 engaged with inferior component 120 and second section 256 engaged with superior component 160. In some embodiments, first section 252 is translationally connected to inferior component 120 such that it slides within recess 128. Such arrangement allows translational movement between inferior component 120 and superior component 160. First section 252 comprises plurality of teeth 254 and second section 256 comprises plurality of teeth 258 operatively arranged to engage plurality of teeth 254. The engagement of teeth 258 with teeth 254 allows superior component 160 to be displaced away from inferior component 120 (i.e., in axial direction AD1) but prevents superior component 160 from being displaced toward inferior component 120 (i.e., in axial direction AD2). Thus, ratcheting expansion mechanism 250 provides a locking feature. It should be appreciated that ratcheting expansion mechanism 250 can be used in place of or in addition to inflatable sac 150.

Figure 10:
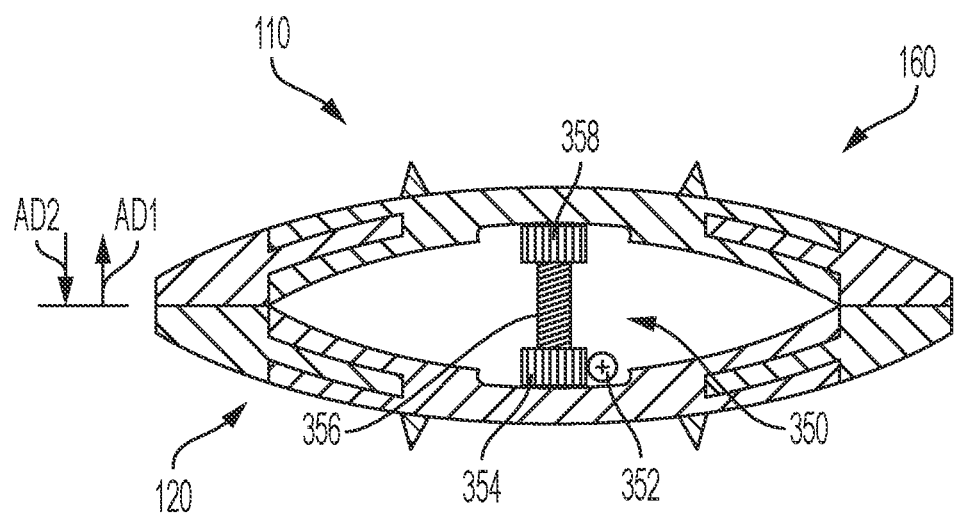
FIG. 10 is a cross-sectional view of the expandable total disc replacement implant taken generally along line 8A-8A in FIG. 7A.

FIG. 10 is a cross-sectional view of implant 110 taken generally along line 8A-8A in FIG. 7A. FIG. 10 shows expansion mechanism or screw jack or worm drive 350. Screw jack 350 comprises worm screw 352, worm wheel 354 engaged with worm screw 352, shaft 356 non-rotatably connected to worm wheel 354, and translating nut 358 engaged with shaft 356 and connected to superior component 162. Worm screw 352 comprises threading that engages gear teeth on worm wheel 354. Rotating worm screw 352 causes worm wheel 354 and shaft 356 to rotate. Shaft 356 comprises threading that threadably engages translating nut 358. As shaft 356 rotates in a first direction translating nut 358 and thus superior component 160 displaces in axial direction AD1. As shaft 356 rotates in a second direction, opposite the first direction, translating nut 358 and thus superior component 160 displaces in axial direction AD2. In some embodiments, translating nut 358 is non-rotatably connected to superior component 160. It should be appreciated that screw jack 350 can be used in place of or in addition to ratcheting expansion mechanism 250 and/or inflatable sac 150. In some embodiments, the expansion mechanism of implant 110 comprises a scissor jack.

Figure 11:
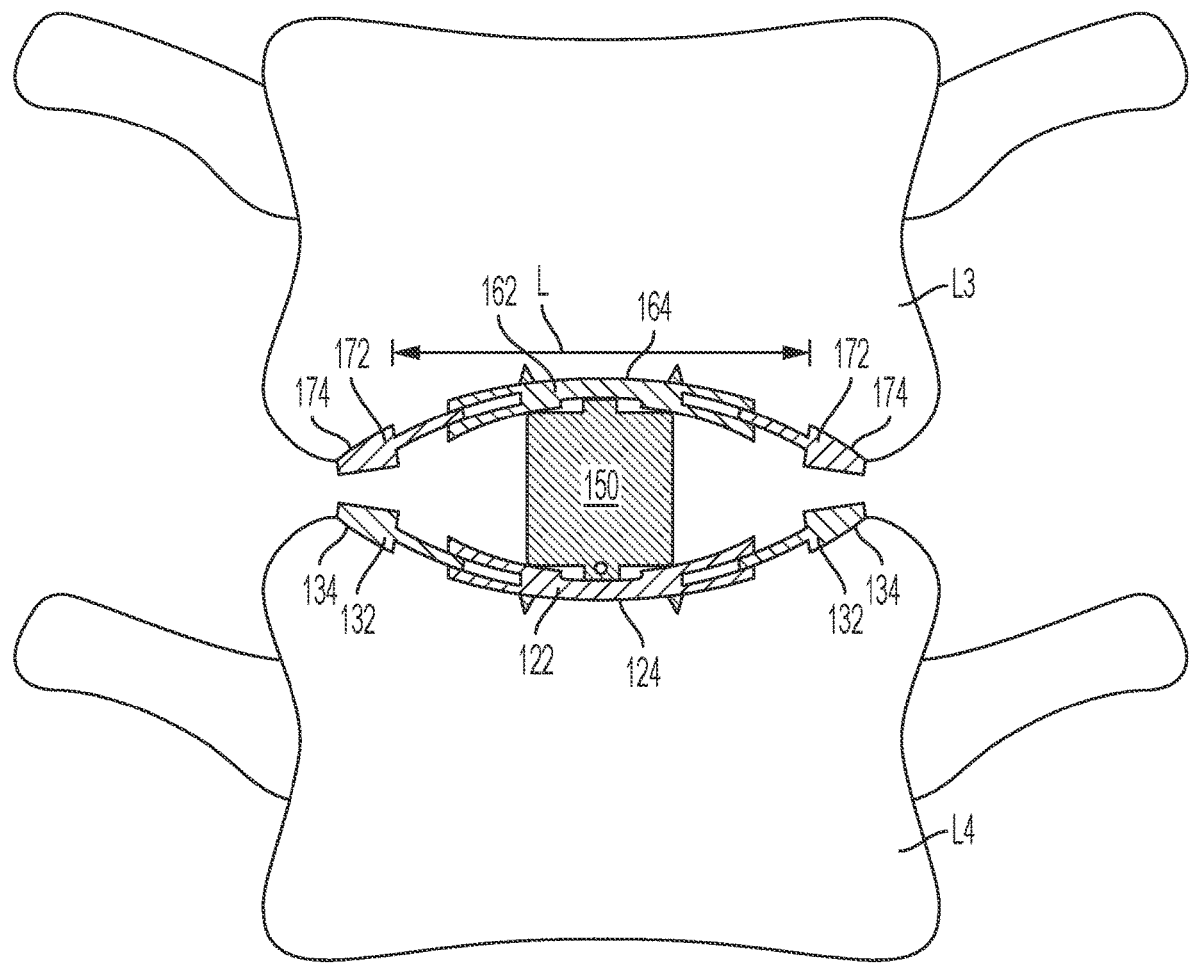
FIG. 11 is a cross-sectional view of the expandable total disc replacement implant shown in FIG. 7B, engaged with vertebrae.
Figure 12A:
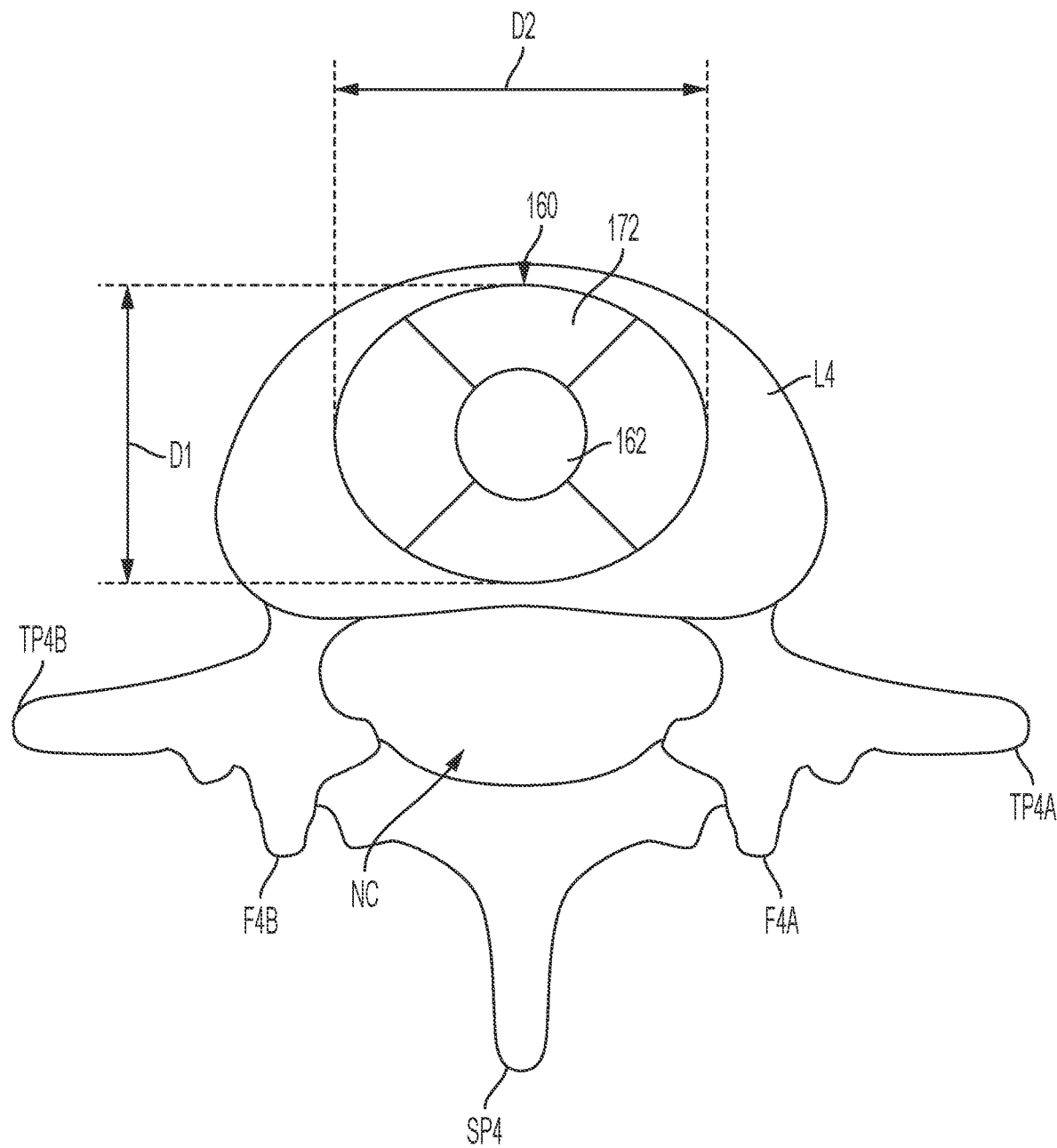
FIG. 12A is a top elevational view of the expandable total disc replacement implant engaged with vertebrae, in a collapsed state.
Figure 12B:
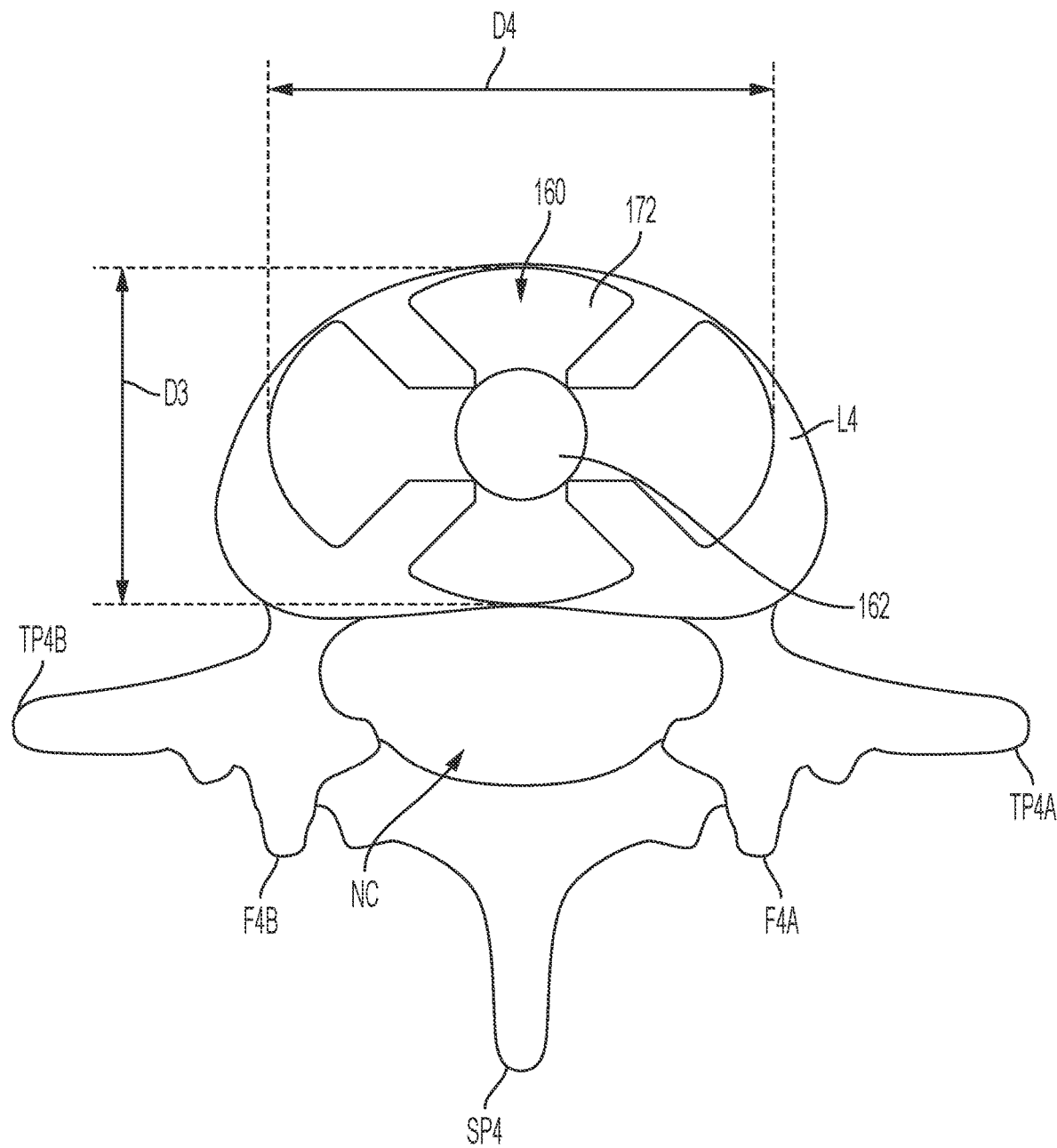
FIG. 12B is a top elevational view of the expandable total disc replacement implant engaged with vertebrae, in an expanded state.

FIG. 11 is a cross-sectional view of implant 110 engaged with vertebrae L3 and L4. FIG. 12A is a top elevational view of implant 110 engaged with vertebra L4, in a collapsed state. FIG. 12B is a top elevational view of implant 110 engaged with vertebra L4, in an expanded state.

To insert implant 110 into a patient, implant 110 should be arranged in the fully collapsed position, as shown in FIGS. 7A and 8A. Implant 110 is then implanted in the disc space between vertebrae, for example, vertebra L3 and vertebra L4, or where disc $D_{L3-L4}$ should be. In some embodiments, and as shown in FIG. 12A, in the collapsed position, implant 110 may be ovular and comprise diameter D1 along the short axis and diameter D2 along the long axis, wherein D2 is greater than D1. In some embodiments, implant 110 comprises a circular geometry. It should be appreciated that implant 110 may comprise any suitable geometry, for example, square, rectangular, ellipsoidal, triangular, trapezoidal, etc.

Once positioned between vertebrae L3 and L4, implant 110 can then be radially expanded as desired. For example, arms 132 and arms 172 are expanded radially outward with respect to core 122 and core 162, respectively, to the desired diameter. For example, implant 110 may be radially expanded such that it comprises diameter D3 along the short axis and diameter D4 along the long axis, wherein D4 is greater than D3. As previously described, the radial expansion of superior component 160 and inferior component 120 is customizable in a plurality of radial directions, for example, radial directions RD1-4.

Once arms 132 and 172 are arranged in their desired positions, expansion mechanism 150, 250, 350 is vertically expanded to displace superior component 160 away from inferior component 120, or vice versa. Expansion mechanism 150, 250, 350 is expanded until the desired height is reached, for example such that implant 110 comprises the height of the original disc for which it is replacing, and left in situ. It should be appreciated that implant 110 may be expanded prior to insertion, or after insertion. In some embodiments, implant 110 is then filled with fusion material, for example, between superior component 160 and inferior component 120.

Figure 13A:
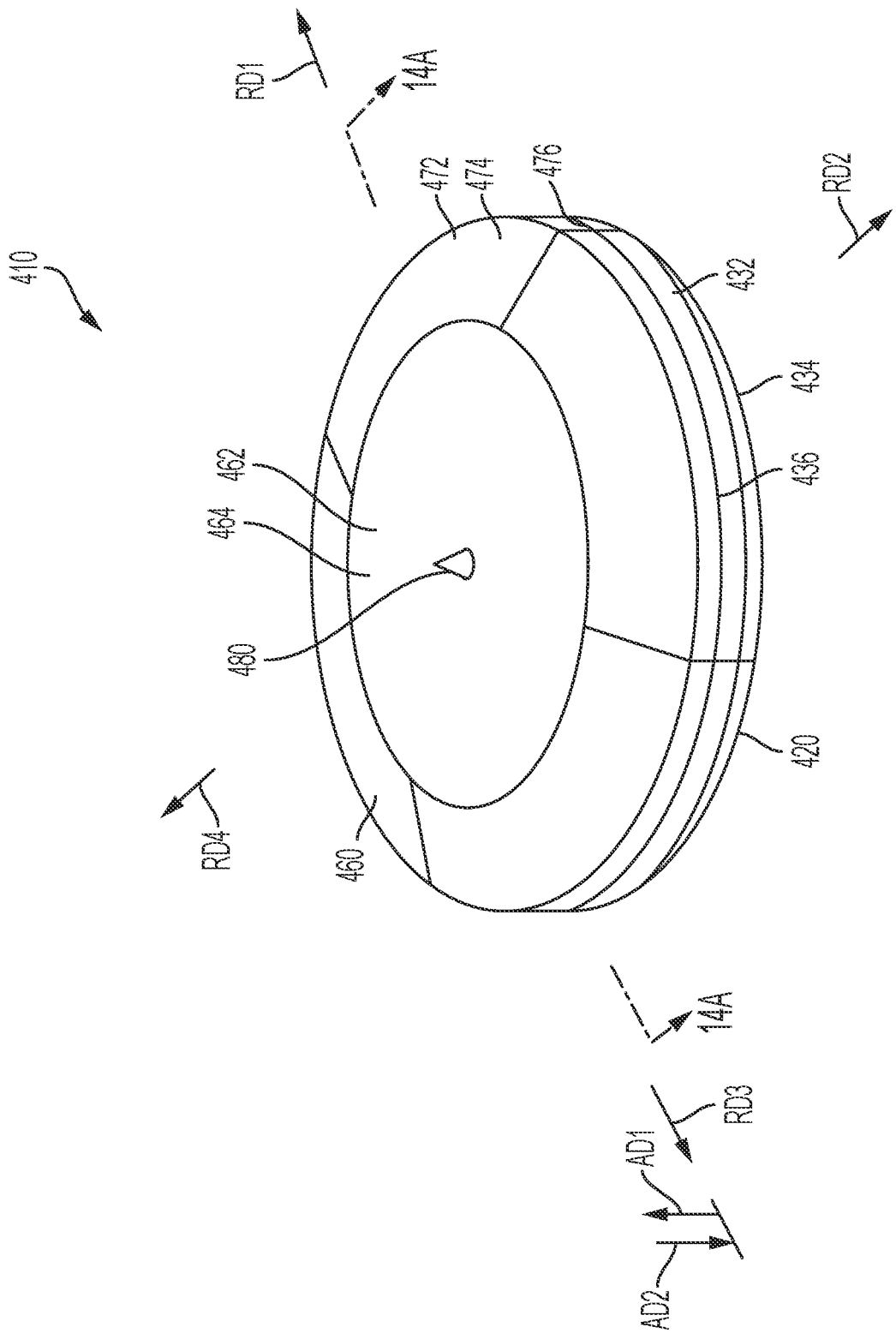
FIG. 13A is a front perspective view of an expandable total disc replacement implant, in a collapsed state.
Figure 13B:
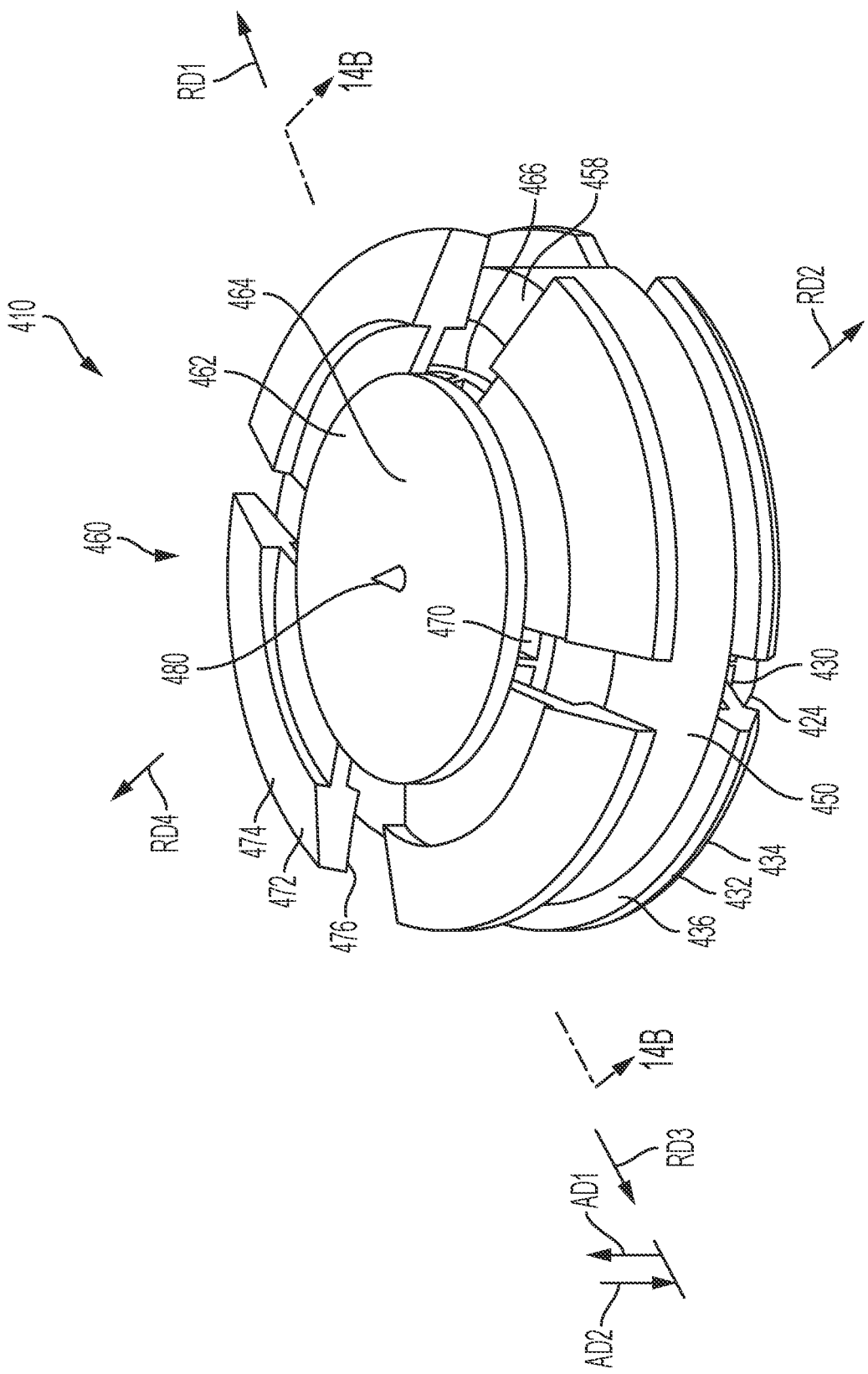
FIG. 13B is a front perspective view of the expandable total disc replacement implant shown in FIG. 13A, in an expanded state.
Figure 14A:
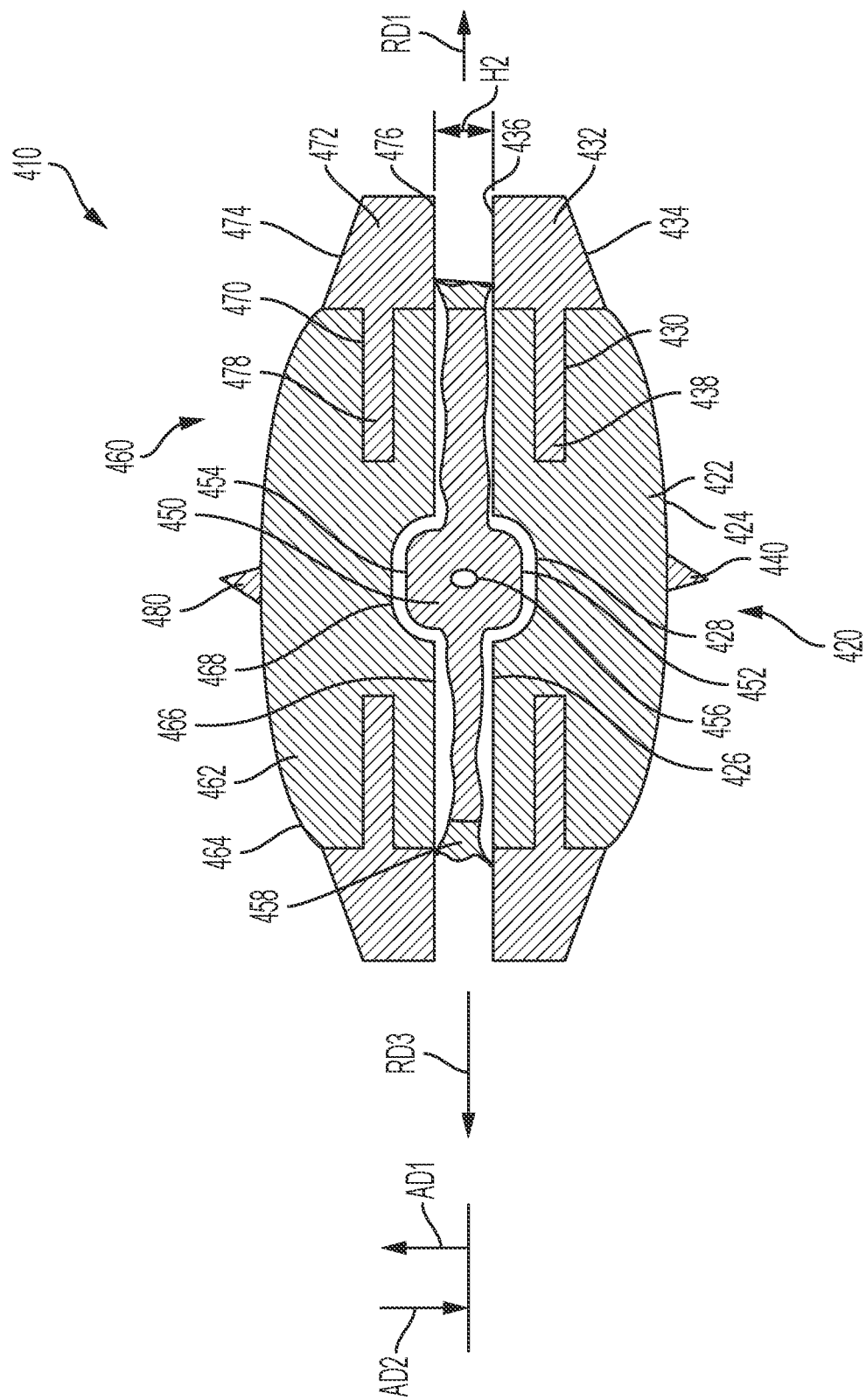
FIG. 14A is a cross-sectional view of the expandable total disc replacement implant taken generally along line 14A-14A in FIG. 13A; and, FIG. 14B is a cross-sectional view of the expandable total disc replacement implant taken generally along line 14B-14B in FIG. 13B.

FIG. 13A is a front perspective view of expandable total disc replacement implant 410, in a collapsed state. FIG. 13B is a front perspective view of expandable total disc replacement implant 410, in an expanded state. FIG. 14A is a cross-sectional view of expandable total disc replacement implant 410 taken generally along line 14A-14A in FIG. 13A. FIG. 13B is a cross-sectional view of expandable total disc replacement 410 implant taken generally along line 14B-14B in FIG. 13B. Expandable total disc replacement implant 410, or implant 410, generally comprises inferior component 420, superior component 460, and an expansion mechanism, for example, expansion mechanism 450. The following description should be read in view of FIGS. 14A-14B.

Inferior component 420 comprises core 422 and one or more arms 432 slidingly and/or telescopingly engaged with core 422. In some embodiments, and as best shown in FIGS. 13A-B, inferior component 420 comprises four arms 432. Core 422 comprises outer surface 424, inner surface 426, recess 428, and one or more apertures 430. Outer surface 424 generally faces radially outward and is operatively arranged to engage an adjacent vertebra. Inner surface 426 generally faces radially inward, or toward superior component 460. Inner surface 426 comprises recess 428 operatively arranged to engage expansion mechanism 450. The engagement of expansion mechanism 450 with recess 428 limits radial displacement of inferior component 420 with respect to expansion mechanism 450. In some embodiments, expansion mechanism 450 is translationally connected to inferior component 420 such that it slides within recess 428. Such arrangement allows translational movement between inferior component 420 and superior component 460. Apertures 430 are arranged radially within core 422. Specifically, apertures 430 extend from an outermost perimeter of core 422 radially inward. In some embodiments, and as shown, apertures 430 reside between and spaced apart from outer surface 424 and inner surface 426. Apertures 430 allow arms 432 to be telescopingly and/or slidingly engaged with core 422. In some embodiments, core 422 comprises four apertures 430 to engage with four arms 432.

Each of arms 432 comprises outer surface 434, inner surface 436, and protrusion 438. Outer surface 434 generally faces radially outward and is operatively arranged to engage with an adjacent vertebra. In some embodiments, in a fully collapsed state, outer surface 434 is aligned with outer surface 424 so as to create a smooth continuous outer surface of inferior component 420. Inner surface 436 generally faces radially inward or toward superior component 460. In some embodiments, in the fully collapsed state, inner surface 436 engages and/or abuts against inner surface 476 of arms 472 (of superior component 460). The engagement of surfaces 436 and 476 and the alignment of surfaces 434 and 424, in the fully collapsed state, prevent ingress of material into implant 410 during insertion and also facilitates easier implantation by providing a smooth and continuous outer implant surface. It should be appreciated that FIG. 14A shows a collapsed state wherein superior component 460 and inferior component 420 are separated by height H2, wherein height H2 is greater than zero. In the fully collapsed state, as described above, height H2 is equal to zero and thus surface 436 abuts against surface 476.

Protrusion 438 is a generally radially extending element that engages aperture 430. In some embodiments, and as shown, protrusion 438 is arranged between and spaced apart from outer surface 434 and inner surface 436. The engagement of protrusion 438 and aperture 430 creates the telescoping and/or sliding connection between arm 432 and core 422, which allows inferior component 420 to be expanded radially in a plurality of directions. In some embodiments, core 422 and/or arms 432 are flexible or elastically deformable which allows inferior component 420 to form to the adjacent vertebra for optimal engagement therewith. In some embodiments, outer surface 424 and/or outer surface 434 comprises one or more projections, for example projection 440, operatively arranged to fixedly secure inferior component 420 to the adjacent vertebra.

Superior component 460 comprises core 462 and one or more arms 472 slidingly and/or telescopingly engaged with core 462. In some embodiments, and as best shown in FIGS. 13A-B, superior component 460 comprises four arms 472. Core 462 comprises outer surface 464, inner surface 466, recess 468, and one or more apertures 470. Outer surface 464 generally faces radially outward and is operatively arranged to engage an adjacent vertebra. Inner surface 466 generally faces radially inward, or toward inferior component 420. Inner surface 466 comprises recess 468 operatively arranged to engage expansion mechanism 450. The engagement of expansion mechanism 450 with recess 468 limits radial displacement of superior component 460 with respect to expansion mechanism 450. In some embodiments, expansion mechanism 450 is translationally connected to superior component 460 such that it slides within recess 468. Such arrangement allows translational movement between superior component 460 and inferior component 420. Apertures 470 are arranged radially within core 462. Specifically, apertures 470 extend from an outermost perimeter of core 462 radially inward. In some embodiments, and as shown, apertures 470 reside between and spaced apart from outer surface 464 and inner surface 466. Apertures 470 allow arms 472 to be telescopingly and/or slidingly engaged with core 462. In some embodiments, core 462 comprises four apertures 470 to engage with four arms 472.

Each of arms 472 comprises outer surface 474, inner surface 476, and protrusion 478. Outer surface 474 generally faces radially outward and is operatively arranged to engage with an adjacent vertebra. In some embodiments, in the fully collapsed state, outer surface 474 is aligned with outer surface 464 so as to create a smooth continuous outer surface of superior component 460. Inner surface 476 generally faces radially inward or toward inferior component 420. In some embodiments, in the fully collapsed state, inner surface 476 engages and/or abuts against inner surface 436 of arms 432 (i.e., height H2 is equal to zero). The engagement of surfaces 476 and 466 and the alignment of surfaces 474 and 464, in the fully collapsed state, prevent ingress of material into implant 410 during insertion and also facilitates easier implantation by providing a smooth and continuous outer implant surface. Protrusion 478 is a generally radially extending element that engages aperture 470. In some embodiments, and as shown, protrusion is arranged between and spaced apart from outer surface 474 and inner surface 476. The engagement of protrusion 478 and aperture 470 creates the telescoping and/or sliding connection between arm 472 and core 462, which allows superior component 460 to be expanded radially in a plurality of directions.

In some embodiments, core 462 and/or arms 472 are flexible or elastically deformable which allows superior component 460 to form to the adjacent vertebra for optimal engagement therewith. In some embodiments, outer surface 464 and/or outer surface 474 comprises one or more projections, for example projection 480, operatively arranged to fixedly secure superior component 460 to the adjacent vertebra.

Expansion mechanism or inflatable balloon or inflatable sac 450 is generally an inflatable device operatively arranged to be filled with material to displace superior component 460 with respect to inferior component 420, or vice versa. In some embodiments, inflatable sac 450 comprises an elastomer, such as rubber. In some embodiments, inflatable sac 450 comprises a nonelastic material. Inflatable sac 450 comprises first end 452, second end 454, and port 456. First end 452 is operatively arranged to engage inner surface 426, specifically recess 428, of inferior component 420 and end 454 is operatively arranged to engage inner surface 466, specifically recess 468, of superior component 460. In some embodiments, end 452 is pivotably connected to inferior component 420 and/or end 454 is pivotably connected to superior component 460. Such pivotable and/or slidable connection between inferior component 420, superior component 460, and expansion mechanism 450 allows general movement and flexion between inferior component 420 and superior component 460, mimicking the normal movement between vertebrae via a disc. Additionally, the elastic properties of cores 422 and 462 and arms 432 and 472 allow further natural movement between vertebrae. In some embodiments, end 452 is fixedly secured to inferior component 420 and/or end 454 is fixedly secured to superior component 460.

Figure 14B:
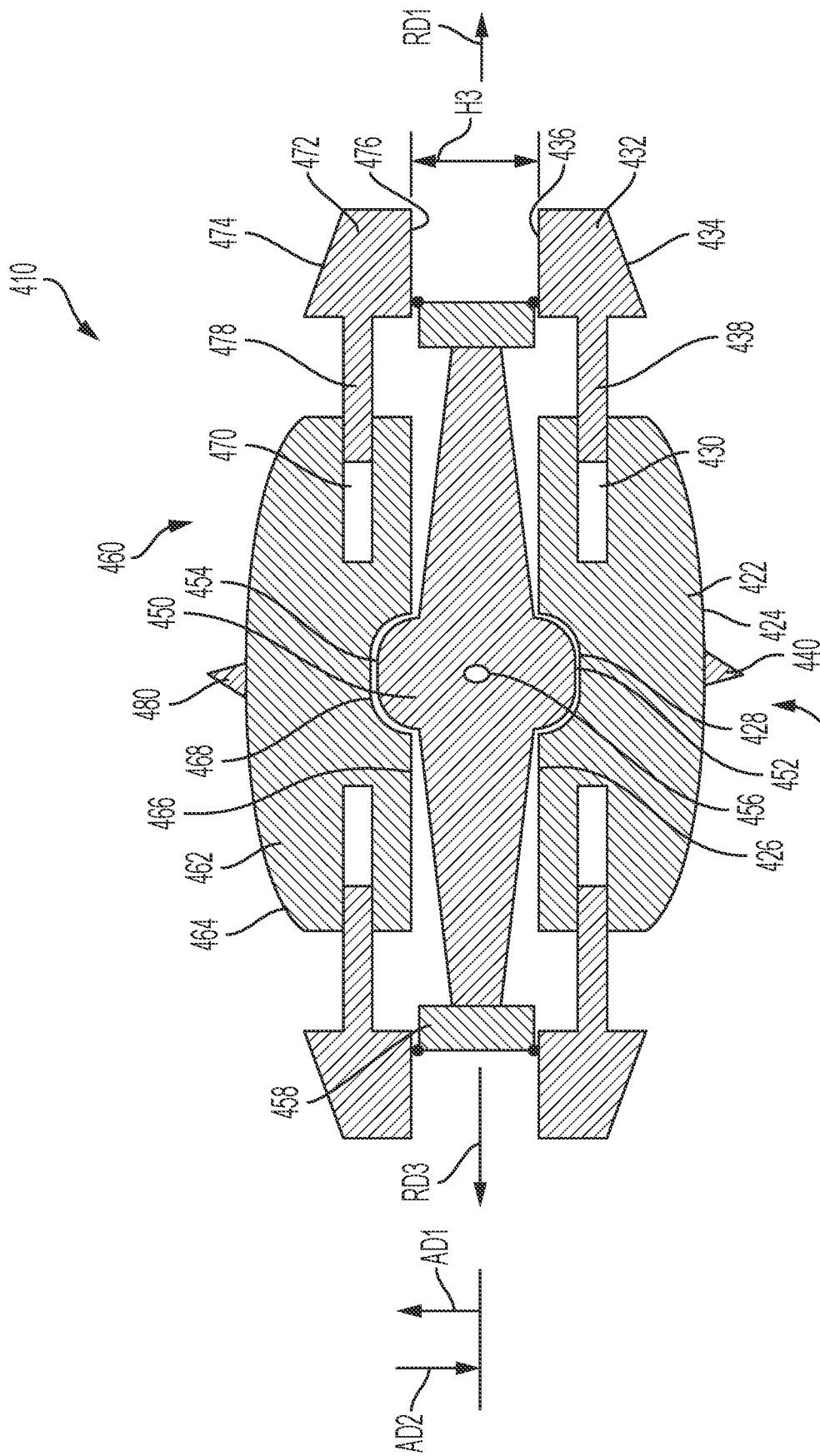

As best shown in FIGS. 14A-B, inflatable sac 450 is slidably and/or pivotably connected to cores 422 and 462 via ends or end projections 452 and 454, respectively. Additionally, inflatable sac 450 is connected to arms 432 and 472. For example, end 452 is connected to arms 432. In some embodiments, end 452 is connected to inner surfaces 436. End 454 is connected to arms 472. In some embodiments, end 454 is connected to inner surfaces 476. In some embodiments, the points of connection between inflatable sac 450 and arms 432 and 472 is at or proximate an outer perimeter of inflatable sac 450. Such arrangement is advantageous because expansion of inflatable sac 450 results not only in vertical expansion but also radial expansion of implant 410, as will be described in greater detail below.

In some embodiments, end projections 452 and 454 comprise a curvilinear surface that engages respective curvilinear surfaces of recesses 428 and 468. This engagement provides not only a ball and socket joint between inflatable sac 450 and superior and inferior components 420 and 460, but also still allows for translational movement between the components since, at least in some embodiments, the radius of curvilinear surfaces 452 and 454 are less than the radius of curvilinear surfaces 428 and 468, respectively. The various curvilinear surfaces may be spherical, ovular, ellipsoidal, or any suitable geometric shape to allow for pivotable and translational displacement between inferior component 420 and superior component 460, and inflatable sac 450.

In some embodiments, inflatable sac 450 comprises end portion 458 arranged on its lateral edge. End portion 458 may be separate from inflatable sac 450 such that material injected into inflatable sac 450 through port 456 will not enter end portion 458. End portion 458 is connected to arms 432 and 472 and comprises an elastic material operatively arranged to, in the fully expanded state of implant 410 as shown in FIG. 14B, allows superior component 160 to displace relative to inferior component 120. For example, end portion 458 may comprise an elastomer, polyglycolic or polylactic acid, rubber, etc. In some embodiments, inflatable sac 450 tapers from its center point to end portion 458 to allow for greater displacement of inferior component 120 and superior component 160 relative to inflatable sac 450.

Material, such as a hardenable polymer, acrylic, PMMA, a viscoelastic polymer, polyurethane, or any other suitable material, is injected into inflatable sac 450 through port 456. As material is injected into inflatable sac 450, inflatable sac 450 expands and superior component 460 is displaced away from inferior component 420. As material is removed from inflatable sac 450, inflatable sac 450 may contract and superior component 460 is capable of displacing toward inferior component 420.

As previously described, in a fully collapsed state, surfaces 476 engage and/or abut against surfaces 436. It should be appreciated, that in some embodiments, a gap or aperture is arranged in implant 410 such that the expansion mechanism 450 therein is accessible in the fully collapsed state. For example, port 156 would be accessible in the fully collapsed state such that implant 110 can be expanded. In some embodiments, in a collapsed or fully collapsed state, as shown in FIG. 14A, superior component 460, specifically surface 476, is separated from inferior component 420, specifically surface 436, by height H2, which is greater than zero to allow accessibility to port 456. In the expanded state, wherein superior component 460 is displaced in axial direction AD1 with respect to inferior component 420, as best shown in FIG. 14B, surfaces 476 are separated from surfaces 436 by height H3, which is greater than height H2. This expansion (i.e., in axial direction AD1) is referred to herein as axial or vertical expansion.

Implant 410 is also capable of radial expansion, for example, in radial directions RD1-4. Arms 432 and arms 472 can be displaced radially with respect to cores 422 and 462, respectively. For example, one of arms 432 and one of arms 472 can be displaced in radial direction RD1 with respect to cores 422 and 462, respectively, one of arms 432 and one of arms 472 can be displaced in radial direction RD3, opposite radial direction RD1, with respect to cores 422 and 462, respectively, one of arms 432 and one of arms 472 can be displaced in radial direction RD2 with respect to cores 422 and 462, respectively, and one of arms 432 and one of arms 472 can be displaced in radial direction RD4, opposite radial direction RD2, with respect to cores 422 and 462, respectively. In some embodiments, radial direction RD2 is arranged perpendicular to radial direction RD1. It should be appreciated that each of arms 432 and 472 are displaceable with respect to each other, allowing for a completely customizable radial expansion. Such customizable radial expansion allows implant 410 to be formed to the exact shape of the patient's vertebra. For example, a patient may have vertebra L4 that is larger than vertebra L3, and thus arms 472 of superior component 460 should be radially expanded less than arms 432 of inferior component 420.

To insert implant 410 into a patient, implant 410 should be arranged in a collapsed or fully collapsed position, for example, as shown in FIGS. 13A and 14A. Implant 410 is then implanted in the disc space between vertebrae, for example, vertebra L3 and vertebra L4, or where disc $D_{L3-L4}$ should be. In some embodiments, in the collapsed position, implant 410 may comprise any suitable geometry, for example, ovular, circular, square, rectangular, ellipsoidal, triangular, trapezoidal, etc.

Once positioned between vertebrae L3 and L4, implant 410 can then be axially and radially expanded. For example, inflatable sac 450 is inflated causing axial expansion, namely, displacing superior component 460 away from inferior component 420, or vice versa. At the same time of axial expansion, inflatable sac 450 expands and displaces arms 432 and 472 radially, for example in radial direction RD1 and radial direction RD3, with respect to cores 422 and 462, respectively. As such, inflation of inflatable sac 450 results in implant 410 expanding axially to the desired height, such that implant 410 comprises the height of the original disc for which it is replacing, and radially to the desired diameter and shape (e.g., ovular, circular, etc.), such that implant 410 comprises the dimensions and shape of the original disc for which it is replacing, and left in situ. It should be appreciated that implant 410 may be expanded prior to insertion, or after insertion. In some embodiments, implant 410 is then filled with fusion material, for example, between superior component 460 and inferior component 420.

It will be appreciated that various aspects of the disclosure above and other features and functions, or alternatives thereof, may be desirably combined into many other different systems or applications. Various presently unforeseen or unanticipated alternatives, modifications, variations, or improvements therein may be subsequently made by those skilled in the art which are also intended to be encompassed by the following claims.

REFERENCE NUMERALS

A Annulus
C Coccyx
C1-C7 Cervical vertebrae
$D_{L1-L2}$ Disc
$D_{L2-L3}$ Disc
$D_{L3-L4}$ Disc
$D_{L4-L5}$ Disc
F Facet
FJ Facet joint
IF Intervertebral foramen
L1-L5 Lumbar vertebrae
N Nucleus
NC Neural canal
S Sacrum
SP Spinous process
TP Transverse process
T1-T12 Thoracic vertebrae
10 Spinal column
110 Expandable intervertebral total disc replacement implant
120 Inferior component
122 Core
124 Outer surface
126 Inner surface
128 Recess
130 Aperture
132 Arm
134 Outer surface
136 Inner surface
138 Protrusion
140 Projections
150 Expansion mechanism or inflatable sac or balloon
152 End 154 End
156 Port
160 Superior component
162 Core
164 Outer surface
166 Inner surface
168 Recess
170 Aperture
172 Arm
174 Outer surface
176 Inner surface
178 Protrusion
180 Projections
250 Expansion mechanism or ratchet device
252 Section
254 Teeth
256 Section
258 Teeth
350 Expansion mechanism or screw jack or worm drive
352 Worm screw
354 Worm wheel
356 Shaft
358 Translating nut
410 Expandable intervertebral total disc replacement implant
420 Inferior component
422 Core
424 Outer surface
426 Inner surface
428 Recess
430 Aperture
432 Arm
434 Outer surface
436 Inner surface
438 Protrusion
440 Projection
450 Expansion mechanism or inflatable sac or balloon
452 End
454 End
456 Port
458 End portion
460 Superior component
462 Core
464 Outer surface
466 Inner surface
468 Recess
470 Aperture
472 Arm
474 Outer surface
476 Inner surface
478 Protrusion
480 Projection
AD1 Axial direction
AD2 Axial direction
D1 Diameter
D2 Diameter
D3 Diameter
D4 Diameter
H1 Height
H2 Height
H3 Height
L Length
RD1 Radial direction
RD2 Radial direction
RD3 Radial direction
RD4 Radial direction

What is claimed is:

1. An expandable intervertebral total disc replacement implant, comprising:
an inferior component, including:
a first core comprising a first outer surface and a first inner surface; and
a first arm telescopingly engaged with the first core;
a superior component, including:
a second core comprising a second outer surface and a second inner surface; and
a second arm telescopingly engaged with the second core; and
an expansion mechanism connected to the first core and the second core, and directly secured to at least one arm of the first arm and the second arm;
wherein the expansion mechanism is an inflatable sac;
wherein as the expandable intervertebral total disc replacement implant is expanded, the expansion mechanism:
displaces the superior component in an axial direction with respect to the inferior component; and
displaces the at least one arm radially outward with respect to its respective core.

2. The expandable intervertebral total disc replacement implant as recited in claim 1, wherein the inflatable sac is connected to the at least one arm at an outer perimeter of the inflatable sac.

3. The expandable intervertebral total disc replacement implant as recited in claim 1, wherein the inflatable sac is connected to the first arm and the second arm.

4. The expandable intervertebral total disc replacement implant as recited in claim 1, wherein the expansion mechanism is connected to the first inner surface and the second inner surface.

5. The expandable intervertebral total disc replacement implant as recited in claim 1, wherein the first core comprises a first radially extending aperture and the first arm is engaged with the first radially extending aperture.

6. The expandable intervertebral total disc replacement implant as recited in claim 1, wherein at least one of the first inner surface and the second inner surface comprises a recess, and the expansion mechanism is slidingly engaged with the recess.

7. The expandable intervertebral total disc replacement implant as recited in claim 1, wherein the first arm comprises:
a first protrusion telescopingly engaged with the first core;
a third outer surface; and
a third inner surface, wherein in a fully collapsed state the third outer surface is aligned with the first outer surface to form a first continuous outer surface.

8. The expandable intervertebral total disc replacement implant as recited in claim 7, wherein the second arm comprises:
a second protrusion telescopingly engaged with the second core;
a fourth outer surface; and
a fourth inner surface, wherein in the fully collapsed state the fourth outer surface is aligned with the second outer surface to form a second continuous outer surface.

9. The expandable intervertebral total disc replacement implant as recited in claim 1, wherein:
the superior component is axially displaceable relative to the inferior component;

the first arm is radially displaceable with respect to the first core; and the second arm is radially displaceable with respect to the second core.

10. The expandable intervertebral total disc replacement implant as recited in claim 1, wherein at least one of the inferior component and the superior component are pivotable with respect to the expansion mechanism.

11. An expandable intervertebral total disc replacement implant, comprising:
   an inferior component, including a first core comprising a first outer surface and a first inner surface;
   a superior component, including a second core comprising a second outer surface and a second inner surface;
   an arm telescopingly engaged with at least one of the first core and the second core; and
   an inflatable sac connected to the first core, the second core, and the arm, wherein at least one of the first inner surface and the second inner surface comprises a recess, and the inflatable sac is pivotably engaged with the recess;
   wherein the inflatable sac is operatively arranged to displace:
      the superior component in an axial direction with respect to the inferior component; and
      the arm in a radial direction with respect to its respective core.

12. The expandable intervertebral total disc replacement implant as recited in claim 11, wherein the inflatable sac is slidably connected to the first inner surface and the second inner surface.

13. The expandable intervertebral total disc replacement implant as recited in claim 11, wherein the first core comprises an aperture extending in the radial direction and the arm is engaged with the aperture.

14. The expandable intervertebral total disc replacement implant as recited in claim 11, wherein at least one of the inferior component and the superior component are pivotable with respect to the inflatable sac.

15. An expandable intervertebral total disc replacement implant, comprising:
   an inferior component, including a first core comprising a first outer surface and a first inner surface;
   a superior component, including a second core comprising a second outer surface and a second inner surface;
   an arm telescopingly engaged with at least one of the first core and the second core; and
   an expansion mechanism connected to the first core and the second core, and secured to the arm, wherein at least one of the inferior component and the superior component are pivotable with respect to the expansion mechanism;
   wherein to expand the expandable intervertebral total disc replacement implant, the expansion mechanism is operatively arranged to displace:
      the superior component in an axial direction with respect to the inferior component; and
      the arm in a radially outward direction with respect to its respective core.

* * * * *